(12) United States Patent
Suzuki

(10) Patent No.: US 6,424,692 B1
(45) Date of Patent: *Jul. 23, 2002

(54) MEDICAL IMAGE PROCESSING WITH CONTROLLED IMAGE-DISPLAY ORDER

(75) Inventor: Tatsuro Suzuki, Utsunomiya (JP)

(73) Assignee: Kabushiki Kaisha Toshiba, Kawasaki (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/235,381

(22) Filed: Jan. 22, 1999

(30) Foreign Application Priority Data

Jan. 22, 1998 (JP) .......................................... 10-010652
Jan. 20, 1999 (JP) .......................................... 11-012305

(51) Int. Cl.$^7$ ............................................. G01N 23/00
(52) U.S. Cl. ................................. 378/4; 378/19; 378/20
(58) Field of Search ............................... 378/98.2, 4–20

(56) References Cited

U.S. PATENT DOCUMENTS 4,649,555 A    3/1987  Matsubayashi
5,592,523 A  * 1/1997  Tuy et al. ..................... 378/19
5,841,473 A  * 11/1998 Chui et al. ................... 348/390

FOREIGN PATENT DOCUMENTS

| JP | 63-62215   | 12/1988 |
| JP | 2-29330    | 6/1990  |
| JP | 8-147315   | 6/1996  |
| JP | 10-192271  | 7/1998  |

* cited by examiner

Primary Examiner—Craig E. Church
(74) Attorney, Agent, or Firm—Oblon, Spivak, McClelland, Maier & Neustadt, P.C.

(57) ABSTRACT

A diagnostic system is provided to display images in an image-display order complying with a desired scan direction in performing a multi-scan. The system is realized by, by way of example, an X-ray CT scanner. The diagnostic system has a display unit, an element performing scanning with an object to acquire data therefrom, an element producing a plurality of images from the data in a production order, an element displaying on the display unit the plurality of images in a display order, and an element for setting the production order or display order. The production or display order is set in accord with a scan direction along which the slice positions are moved every scan. The production order is, for example, a reconstruction order of the images. The image reconstruction based on the reconstruction order results in that images are displayed in that order, i.e., in an order complying with the scan direction. Of course, the display order itself is set, the images are displayed in that order, i.e., in an order complying with the scan direction.

22 Claims, 21 Drawing Sheets

SCAN DIRECTION "1"

RECONSTRUCTION  A1 A2 A3 A4 A5 B1 B2 B3 B4 B5 C1 C2 C3 C4 C5

DISPLAY         A1 A2 A3 A4 A5 B1 B2 B3 B4 B5 C1 C2 C3 C4 C5
                                                              ⟶ t

SCAN DIRECTION "2"

RECONSTRUCTION  C5 C4 C3 C2 C1 B5 B4 B3 B2 B1 A5 A4 A3 A2 A1

DISPLAY         C5 C4 C3 C2 C1 B5 B4 B3 B2 B1 A5 A4 A3 A2 A1
                                                              ⟶ t

FIG. 11A  FIG. 11B

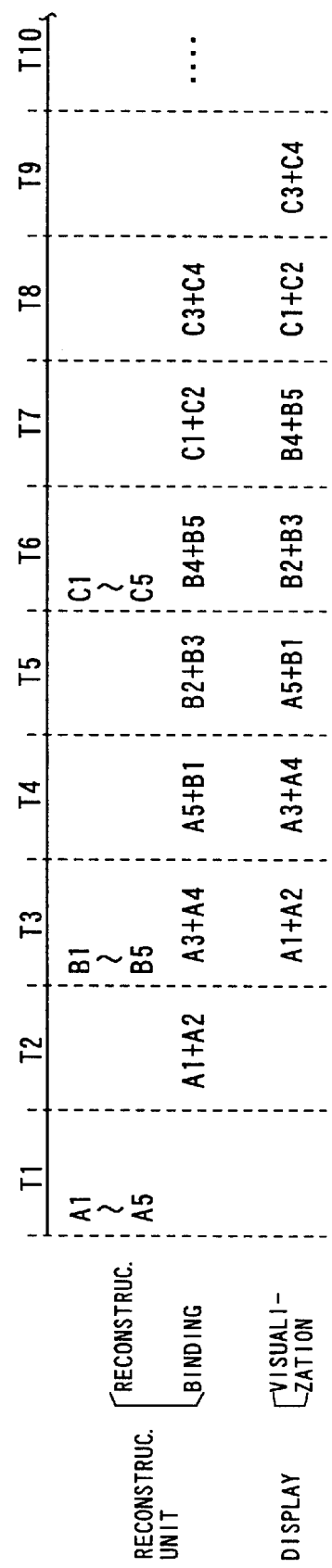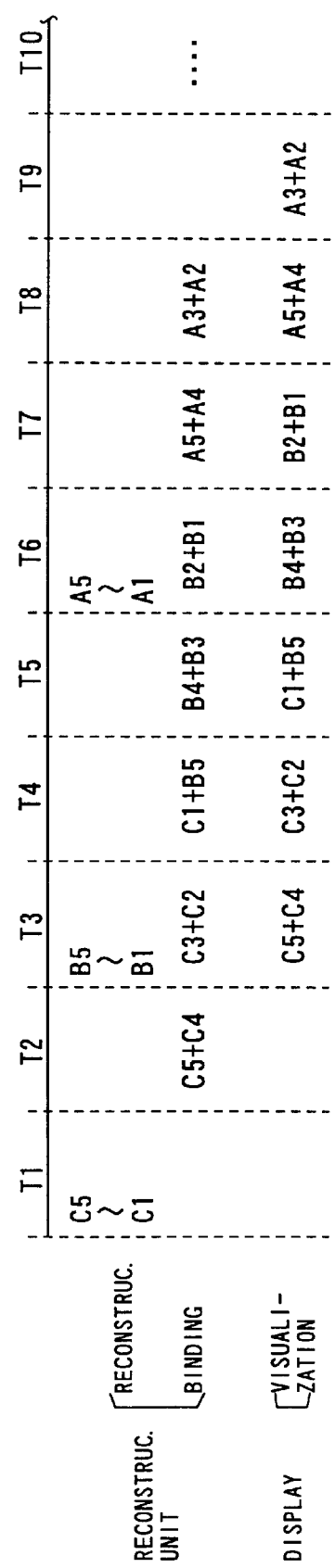
FIG. 16A
FIG. 16B

MEDICAL IMAGE PROCESSING WITH CONTROLLED IMAGE-DISPLAY ORDER

BACKGROUND OF THE INVENTION

The present invention relates to a diagnostic system that provides images of patients (objects) to be interpreted, and particularly tot the diagnostic system that provides the relationship between a direction (scan direction) along which a scan position is moved and an display order of tomographic images is improved. The diagnostic system is realized, for example, by an X-ray CT scanner capable of simultaneously scanning a plurality of slices of an object with scanning positions moved repeatedly, with the result that scan data of a plurality of slices are acquired at each scan position, then a plurality of tomographic images are obtained for diagnosis.

In facilities such as hospitals, an X-ray CT scanner is used as one of medical imaging modalities. The scanner includes two types of scanners referred to as a "single slice CT" and a "multi-slice CT."

The single slice CT scanner is an imaging modality that can provide a single tomographic image by performing a single scan (a one-time scan for acquiring data necessary for image reconstruction). This CT scanner is normally used as follows. At a desired slice position, scanning is performed one time for acquiring raw data (that is, projected X-ray data or original data) of the one slice, then, for example, the tabletop on which a patient lies is moved for the next scan by a length corresponding to its slice thickness measured at the rotational center of an imaging region. At this new scan position, raw data for the adjacent or contiguous slice are acquired again. Repeating this scan and tabletop travel (alternatively, moving of the X-ray tube and X-ray detector) in sequence provides data of a plurality of tomographic images in a desired region of interest at intervals. Reconstructed tomographic images are displayed on a monitor in the reconstructed order. This scan is called "multi-scan."

On one hand, the multi-slice CT scanner is used for providing a plurality of images by the one-time scan. The number of images are usually agreed with that of detecting element rows in the slice direction of a two-dimensional X-ray detector used. For example, if the rows are five in the slice direction, raw data (projected data) of five slices can be acquired by the one-time scan.

The multi-scan can also be applied to multi-slice CT scanners. On having obtained raw data of a plurality of slices by performing the scan one time, the tabletop on which a patient lies is then moved in a scanning direction for the next scan by a length that corresponds to a total thickness of the slices (at the rotational center of an imaging region in the gantry). This can provide at a time raw data of a plurality of slices contiguous to the last plural slices.

The raw data of the plural slices are reconstructed with a given computation technique into a plurality of tomographic images, which are then displayed in the reconstructed order on a monitor. This repetition of scans and moving of the tabletop (or, moving of an X-ray tube and a detector) for a plurality of slices provides at intervals a plurality of tomographic images in a patient's region to be diagnosed.

In CT examination, there is a diagnostic method that allows a doctor or others to interpret displayed tomographic images on a monitor, concurrently with scanning. Additionally, in the conventional CT examination, a direction (hereinafter, referred to as a scan direction) along which the scan position advances in one of the slice directions is normally fixed to a one way, but reversible. For instance, selectively driving a drive unit installed in a patient couch in either of two predetermined ways leads to arbitrary selection of the scan direction in either of a head-to-feet direction or a feet-to-head direction.

In the case that single slice CT scanners adopts a diagnostic method that allows the concurrent execution of imaging (scanning) and interpretation, it is enough that images are reconstructed in the scanned order and reconstructed images are then displayed in sequence, because only one image (tomographic image) is obtained for each scan. That is, independently from the scan directions, the diagnostic method is realized under a constant processing flow along which scanning, reconstruction, and display are carried out consecutively.

However, when such diagnostic method is applied to multi-slice CT scanners, there poses a problem described below.

Conventionally, since the scan direction has been set to one way, raw data of a plurality of slices acquired at a time by the multi-scan are reconstructed in a fixed slice position order advancing in the one way. For example, in each of three multi-scans A to C shown in FIG. 1A or 1D, the reconstructing orders are always set to "slices A1, A2, A3, and A4; slices B1, B2, B3, and B4; and slices C1, C2, C3, and C4." Thus images are reconstructed and displayed in this order.

As understood from the figures, in the case of FIG. 1A, the order of reconstruction and display for slices accords with the scan direction "1" and becomes the order of "A1, A2, A3, A4, B1, B2, . . . ." Because the images appear in the order complying with the scan direction "1", interpreting a plurality of images displayed in turn becomes are easier, providing interpreters three-dimensional, internal structure of a diagnostic region in an easily understandable manner.

In contrast, when the scan direction "2" is selected, the slices in the scan direction "2" proceed in the order of "C4, C3, C2, C1, B4, B3, . . . ," while they are displayed in the order of "C1, C2, C3, C4, B1, B2, . . . ."

In other words, as to image display, slice images farthest from the front in the scan direction precedes those at the frontal side, providing observers (or interpreters) a feeling that the displayed images are spatially reversed. It is therefore difficult for observers to easily understand or grasp an internal structure of a diagnostic region three-dimensionally. This image observation imposes very troublesome, difficult work on observers. There is a fear that accuracy in interpretation may be lowered, in addition to increased interpretation work leading to lower efficiencies in interpretation Furthermore, due to a fixed order to reconstruct and display images, the conventional image display technique is not useful, even if an operator wants to set the order in an arbitrary or highly flexible fashion.

SUMMARY OF THE INVENTION

The present invention has been made in consideration with the above problems. And one object of the present invention is to provide a diagnostic system (by way of example, which is realized by an X-ray CT scanner) capable of displaying images according to a specified or selected scan direction in performing the multi-scan, independently from in which way the scan direction is set, thus facilitating the three-dimensional understanding of an internal structure of a patient's region to be diagnosed.

Another object of the present example is to remarkably enhance flexibility in setting an order along which images are reconstructed and then displayed in the multi-scan.

Still another object of the present invention is to not only remarkably enhance flexibility in setting a scan order along which images are displayed in the multi-scan but also display images along the scan direction, regardless of any scan direction, thus facilitating the three-dimensional understanding of an internal structure of a patient's region to be diagnosed.

In the present invention, an order to reconstruct images (i.e., resulting in the order to reconstruct and display images: referred to as "reconstruction order") and an order to display images (referred to as "display order") are defined. Specifying either one of the reconstruction order or the display order permits images to be displayed on a display or monitor in a desired image-display order of slices scanned. That is, the reconstruction and display orders are parameters to control the image-display order.

In order to achieve the objects, as a first aspect of the invention, there is provided a diagnostic system having a display unit, comprising: means for performing scanning with an object to acquire data therefrom; means for producing a plurality of images from the data in a production order of the images; means for displaying on the display unit the plurality of images in response to producing each image; and means for setting the production order.

It is preferred that the production order setting means sets the production order for the plurality of images in accord with a scan direction along which the slice positions are moved every scan.

Another aspect of the present invention is that a diagnostic system having a display unit, comprising: means for performing scanning with an object to acquire data therefrom; means for producing a plurality of images from the data; means for displaying on the display unit the plurality of images in a display order of the images; and means for setting the display order.

It is preferred that the display order setting means sets the display order for the plurality of images in accord with a scan direction along which the slice positions are moved every scan.

Preferably, the image producing means produces the plurality of images whose slice positions differ from each other per one-time scan performed by the scanning performing means. Still preferably, the scanning performing means performs a plurality of times of scans as the slice positions are moved.

By way of example, the scanning performing means comprises an X-ray source irradiating an X-ray beam toward the object, a two-dimensional detector in which a plurality of arrays of detecting elements are arranged a plurality of rows in a slice direction of which one way is the scan direction for detecting the X-ray beam transmitted through the object, and data acquisition means outputting as the data projection data corresponding to a signal detected by the two-dimensional detector; and the image producing means includes reconstructing means reconstructing the images from the projection data.

For example, in the case of the first aspect, the production order setting means sets a reconstruction order of the images reconstructed by the reconstructing means. In the case of the second aspect, the display order setting means sets an order of the images displayed by the image displaying means.

Still preferably, the scan direction is a direction along which at least one of a tabletop on which the object lies and a gantry in which the scanning performing means is moved.

It is also preferred that the image producing means includes means for mutually binding image data of a plurality of slices contiguous in the plurality of slice positions for outputting as the images to the image displaying means.

It is also preferred that the image displaying means displays on the display unit the images one by one in turn according to the production order or the display order for the images. Still preferred is that the image displaying means displays on the display unit the images in a list mode on the screen thereof according to the production order or the display order for the images.

Therefore, no matte how the scan direction is set, the scanned images can be displayed on a display in a slice position order complying with the scan direction. A situation that images are displayed in the reversed order to the scan direction is surely avoided. A three-dimensional understanding of internal structures of an object's region to be diagnosed can be performed in a steady, speedy and easy manner, contributing to an increase in accuracy of diagnosis and a reduction in operation work.

According to a third aspect of the present invention, provided is a diagnostic system having a display unit, comprising: means for performing scanning with an object to acquire data therefrom; means for producing a plurality of images from the data; means for displaying on the display unit the plurality of images; and means for displaying information about a display order of the images displayed by the image displaying means, the display order resulting from a processing order in either one of the image producing means and the image displaying means.

In this aspect, for example, the display-order information displaying means displays the display order information on the display unit also serving as a console monitor. Also it is preferred to further comprising means for setting the display order into an arbitrary order. By way example, the display-order setting means is means for manually setting as the display order information about a regular or random slice position of the object scanned by the scanning performing means.

Thus an operator is allowed to consider conditions of a region to be diagnosed in the stage of scan planning, and to decide the image-display order arbitrarily or in a flexible manner, based on how the conditions are. The image-display order thus-set can be visually confirmed there.

According to a fourth aspect of the present invention, there is provided a recording medium in which a diagnostic program is recorded, the program is used for achieving means for acquiring data by scanning an object; means for producing from the data a plurality of images; means for displaying the plurality of images; and means for setting an order of the plurality of images displayed by the displaying means, the display order resulting from a processing order in either one of the producing means and the displaying means.

The program recorded in the recording medium can be read by a computer installed in a diagnostic system, such as an X-ray CT scanner. On the basis of the program, the system can operate and provide the forgoing advantages inherently given the present invention.

The remaining features of the invention will be clearly understood from the following description of preferred embodiments and their modifications, described together with accompanying drawings.

BRIEF DESCRIPTION OF THE DRAWINGS

In the accompanying drawings;

FIGS. 11A and 11B pictorially represent in each scan direction an example of the storage format of raw data according to one modification of the first embodiment;

FIGS. 16A and 16B are illustrations of timing among reconstruction, binding processing, and display for each scan direction in one modification of the third embodiment;

DESCRIPTION OF THE PREFERRED EMBODIMENTS

Referring to the accompanying drawings, a variety of embodiments and their modifications of the present invention will now be described. In the following embodiments and modifications, a diagnostic system according to the present invention is practiced, bay way of example, into an X-ray CT scanner.

First Embodiment

Referring to FIGS. 1–9, an X-ray CT scanner of a first embodiment will be explained.

The X-ray CT scanner is characterized, as detailed below, by a structure in which the order to reconstruct acquired data is controlled. Thus, acquired data are provided to a reconstruction unit in the controlled order, then reconstructed images are automatically displayed on a display image by image in the reconstructed order.

Figure 1A:
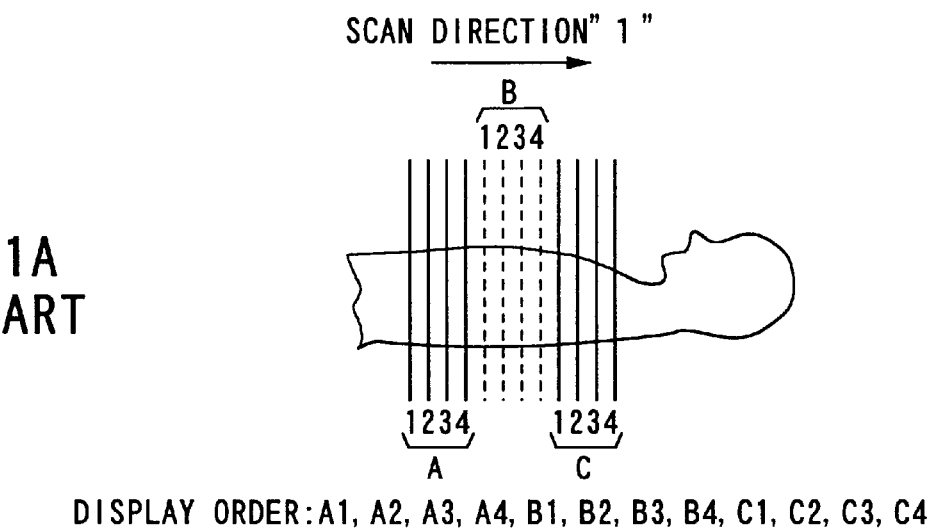
FIGS. 1A and 1B illustrate the conventional relationship between slice positions and the order of image display in each scan direction.
Figure 1B:
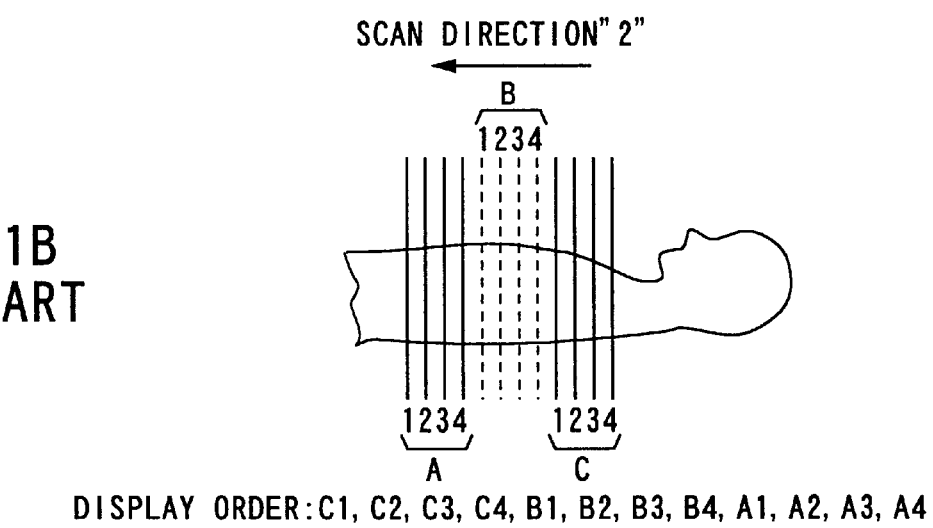
Figure 2:
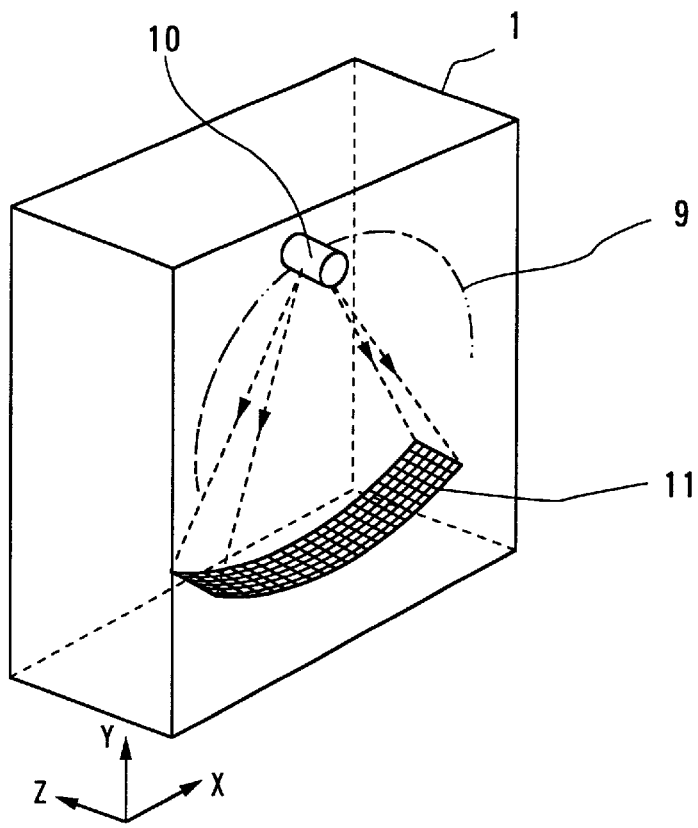
FIG. 2 is a conceptual view illustrating a gantry of an X-ray CT scanner adopted as a diagnostic system according to embodiments of the present invention.

An X-ray CT scanner shown in FIG. 2 comprises a gantry 1, patient couch 2, control cabinet 3, power supply 4, and various controllers 31 to 33, wherein those components are driven on an R-R (rotate-rotate) method. The controllers consists of a high-voltage controller 31, gantry controller 33, and couch controller 32.

Figure 3:
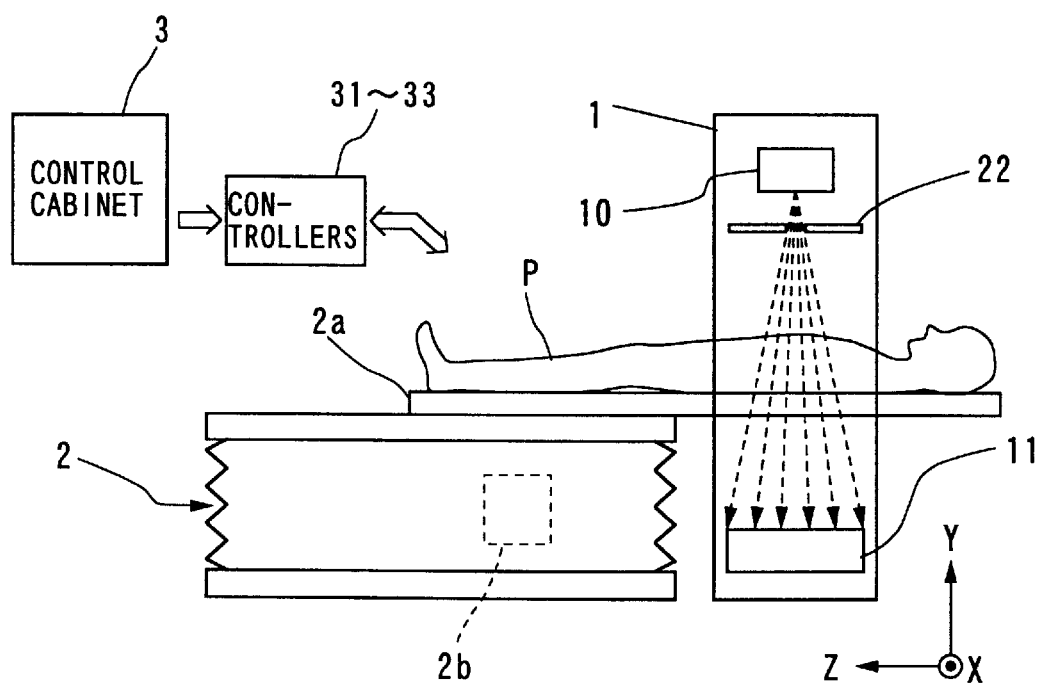
FIG. 3 is a general construction illustrating the gantry, a patient couch, and X-ray beams in the X-ray CT scanner.

In the diagnostic systems as illustrated in FIGS. 2 and 3, the longitudinal direction of the patient couch 2 is defined as a slice direction (or rotation axis direction) Z, and the remaining two directions orthogonal thereto are defined as a channel direction X and an X-ray beam irradiating direction Y.

On the couch 2 is provided a tabletop 2a slidably supported thereon in its longitudinal direction (i.e., slice direction Z), on which a patient P lies. The tabletop 2a is driven by a couch driving unit 2b, represented by a servomotor, so that it can be inserted into a diagnostic bore(not shown) of the gantry 1. The couch driving unit 2b receives a driving signal from the couch controller 32. The couch 2 is also provided with position sensors (not shown), such as encoders, that detect as an electric signal from positions of the tabletop 2a in its longitudinal direction. The detected signal is sent to the couch controller 32 for controlling the couch position.

Figure 4:
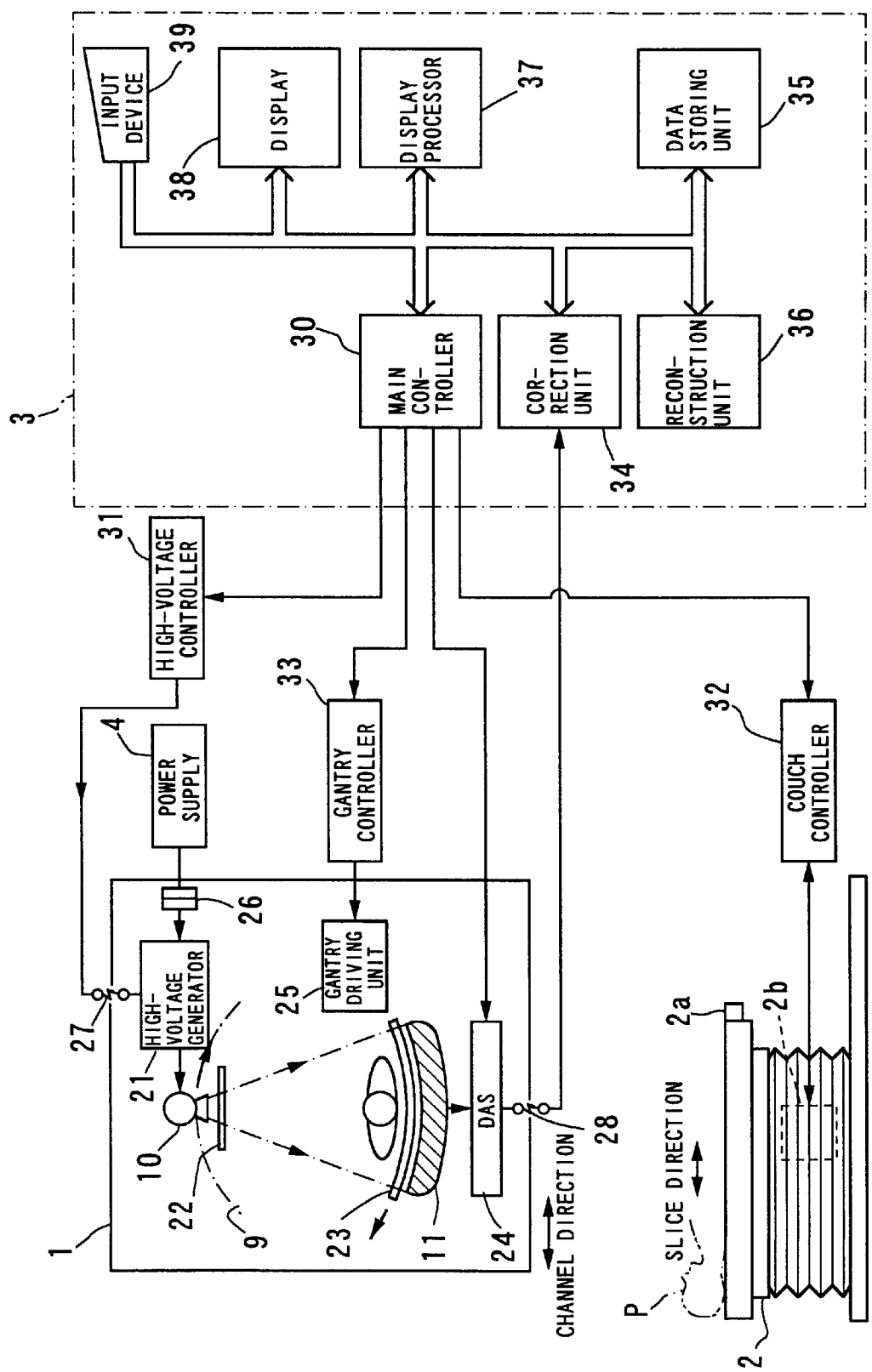
FIG. 4 is a block diagram showing the electric general configuration of the X-ray CT scanner.

The gantry 1 has an approximate cylindrical rotation frame 9 installed therein, as shown in FIGS. 2 and 4. The diagnostic bore exists in an inside space formed by the rotation frame 9. An X-ray tube 10 and an X-ray detector 11 are provided on the rotation frame 9 such that they face with each other through a patient P inserted into the diagnostic bore. Provided around the rotation frame 9 are, as shown in FIG. 4, a high-voltage generator 21, pre-collimator 22, post-collimator 23, data acquisition system (DAS) 24, and gantry driving unit 25.

The X-ray tube 10, serving as an X-ray source, is structured as a rotation anode type of X-ray tube, for example.

The tube 10 has a filament heated by current supplied from the high-voltage generator 21, causing thermal electrons to emit toward a target placed therein. The thermal electrons impinge on the target to produce an effective focus, from which an X-ray beam (fan beam) is irradiated.

Provided to the high-voltage generator 21 is a low-voltage power from the power supply 4 via a low-voltage slip ring 26 as well as a control signal to control X-ray irradiation from the high-voltage controller 31 via an optical signal transmission system 27. The high-voltage generator 21 generates high-voltage power using the supplied low-voltage power, converts the high-voltage power into a pulsed tube voltage signal according to the control signal, and providing it to the X-ray tube 10.

The X-ray detector 11 is composed of a two-dimensional detector where an array consisting of a plurality of detecting elements (corresponding to a plurality of channels) are arranged in a plurality of rows in the slice direction (refer to FIG. 2). Each detecting elements is formed in a solid type of detector that has a combined scintillator and photodiode structure converting incoming transmitted X-rays into corresponding electric current signals. The detected feeble current signals are then sent to the DAS 24. Both the X-ray tube 10 and the X-ray detector 11 are rotated with the rotation frame 9 around the rotation center axis of the diagnostic bore in the gantry 1.

The DAS 24 amplifies and analog-to-digital converts the feeble current signals sent from the detector 11, and provides a data transmission unit 28 with the amplified and digitized data as acquisition data. To realize this operation, the DAS 24 has a construction taking account of the detector 11 formed into a two-dimensional detector. Although not shown, the DAS 24 comprises a data selection unit selecting the detected signals for one line channel by channel from the detection signals of "n-channels×f-element rows (n, f: integers larger than 1)" in response to a line selection signal sent from the main controller, and a data acquisition unit amplifying and analog-to-digital converting the selected detection signals from the data acquisition unit.

The data transmission unit 28 connects signal paths between the rotation side and the fixed side in the gantry 1, and is formed into an optical transmission system capable of performing non-contact signal transmission. A slip-ring transmission system may be used for the unit 28. The digital-form acquisition data, which correspond to the transmitted X-rays through a patient, obtained by way of the data transmission system 28 is supplied to a correction unit installed in the control cabinet 3.

Further the pre-collimator 22 intervenes between the X-ray tube 10 and a patient P, while the post-collimator 23 intervenes between the patient P and the X-ray detector 11. The pre-collimator 22 has a slit-like opening having a constant width in the channel direction X as well as a variable or fixed width in the slice direction Z. An X-ray beam irradiated by the tube 10 is collimated in its width in the slice direction Z, being formed into a fan beam of which slice-directional width matches the total slice width of the detecting element rows of the detector 11. The post-collimator 23 is also a similar slit-like opening to the pre-collimator, and in this example, is in charge of the auxiliary collimation of the X-ray beam once collimated by the pre-collimator 22.

The gantry driving unit 25 has a mechanism, including a motor and gear trains, which rotates the rotation frame 9 around its center axis in the gantry 1. All the rotation-side elements are attached to the rotation frame 9. A drive signal is provided to the gantry driving unit 25 from the gantry controller 33.

The high-voltage controller 31, couch controller 32, and gantry controller 33, which exist between the gantry 1 and couch 2 and the control cabinet 3 from a signal handling viewpoint, response to control signals given by the main controller later described so that each drives loading elements assigned thereto.

The control cabinet 3 has a main controller 30 controlling the entire operation and processing in the system, and a correction unit 34, data storing unit 35, reconstruction unit 36, display processor 37, display 38, and input device all of which are connected through a bus with the main controller 30. A memory not-shown is installed, as a recording medium, in the main controller 30. In the memory is previously recorded a program data for the entire operation and processing of the system. The memory may be placed outside the main controller 30.

The correction unit 34 performs various kinds of correction with the digital-form acquisition data sent from the DAS 24, responsively to a command issued by the main controller 30. The corrected acquisition data are temporarily stored in the data storing unit 35, responsively to a write command from the main controller 30. In response to a reading-out command issued at proper timing from the main controller 30, the stored data are read out from the unit 35, being transferred to the reconstruction unit 36. Under control of the main controller 30, the reconstruction unit 36 reconstructs the received acquisition data slice by slice into tomographic images on the basis of, for example, a convolution backprojection method.

Data of the tomographic images are, under control of the main controller 30, sent to the display processor 37, and if required, stored in the data storing unit 35. The display processor 37 performs necessary processing, such as coloring processing or addition of annotation data and scan information, with the tomographic data, then supplies them to the display 38. In the display 38, the topographic data are digital-to-analog converted and displayed as tomographic images. The input device 39 is placed to give the main controller 30 scan conditions, image display conditions, and others. The scan conditions includes the number and positions of detecting element rows of the detector, a region to be scanned and its position, a slice thickness, an X-ray tube voltage, an X-ray tube current, and a desired scan direction.

The operative explanation will now be given this embodiment system, focusing on advantages resulting from control of the reconstruction order designated in accord with a desired scan direction.

Figure 5A:
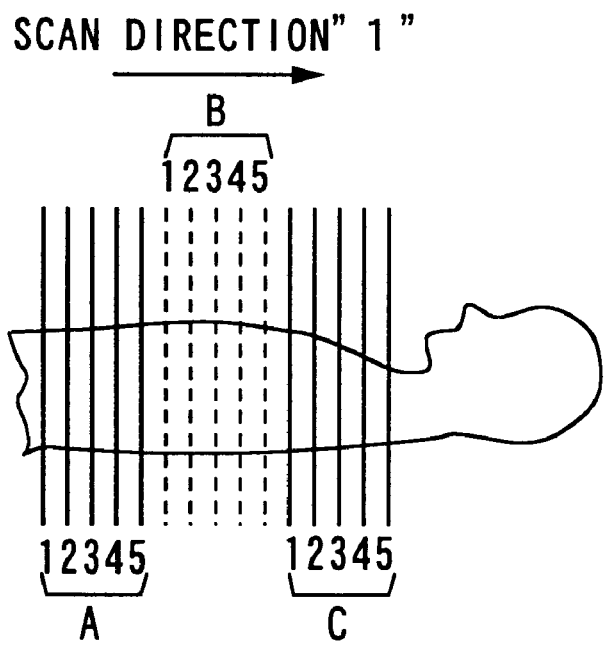
FIGS. 5A and 5B illustrate the relationship between slice positions and each scan direction.
Figure 5B:
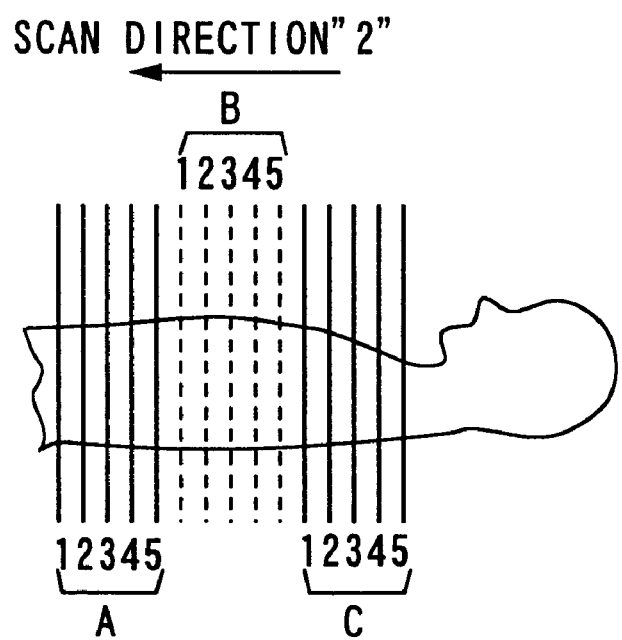

As shown in FIGS. 5A and 5B, multi-scans are performed in a scan direction "1" and/or a scan direction "2". The scan direction is defined as a direction along which a multi-scan is moved in the slice direction Z.

In the case of a multi-scan shown in FIG. 5A, a multi-scan consisting of three-time scans A, B and C are consecutively performed, in this order, in a direction (defined as a scan direction "1") advancing from the feet to the head of a patient (object to be diagnosed) in the body axis direction. In contrast, in the case of a multi-scan shown in FIG. 5B, a multi-scan consisting of three-time scans C, B and A are consecutively performed, in this order, in an opposite direction (defined as a scan direction "2") advancing from the head to the feet of a patient in the body axis direction. Each scan is capable of scanning five slices, for example, at a time. In each scan, the reference numerals 1 to 5 are attached in this order to five slices advancing from the feet to the head.

Figure 6:
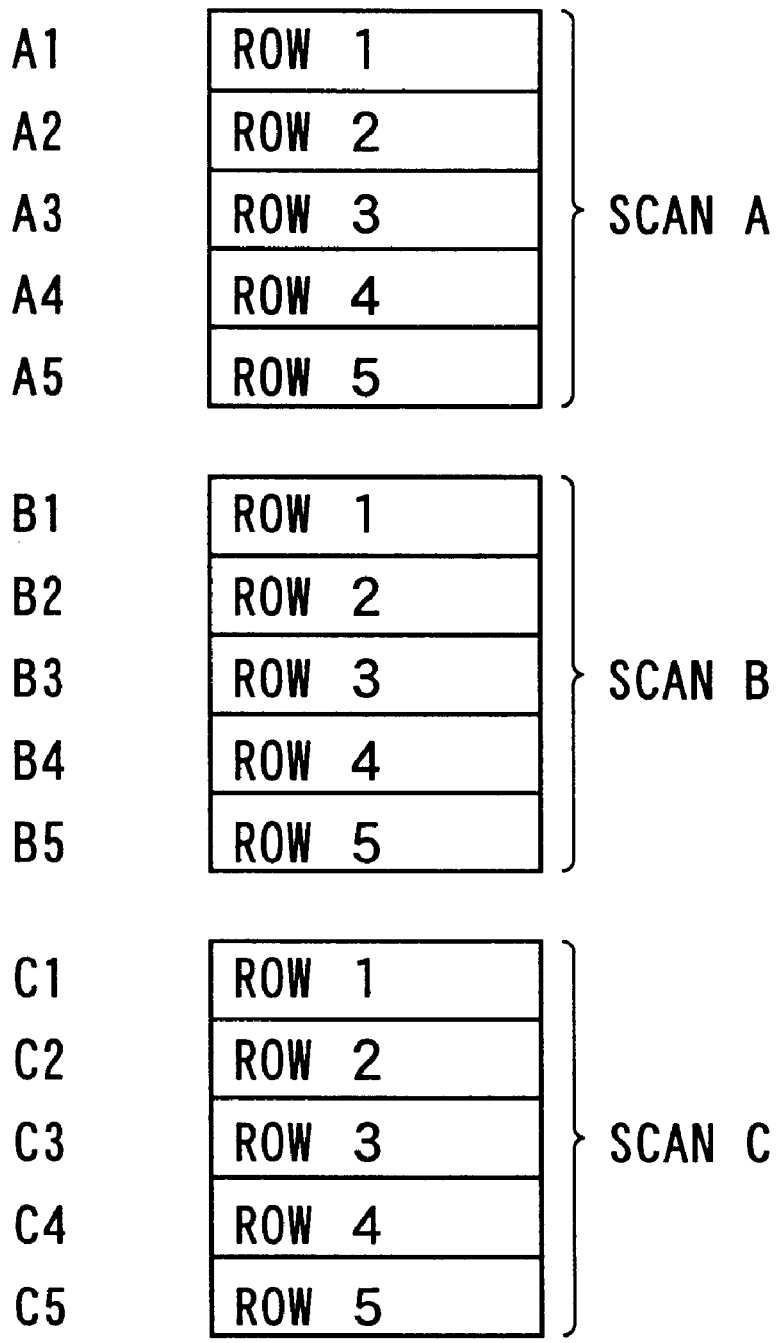
FIG. 6 pictorially shows a storage format of raw data acquired.

Acquisition data (raw data) obtained with the multi-scan in either the scan direction "1" or "2", which come from the DAS 24, are corrected by the correction unit 34, formed into different files for each of the scans A, B and C, and temporarily stored in the data storing unit 35 in a format illustrated in FIG. 6. A data file from a single scan consists of five raw data files for five slices corresponding to five rows or detecting elements, respectively.

Figure 7:
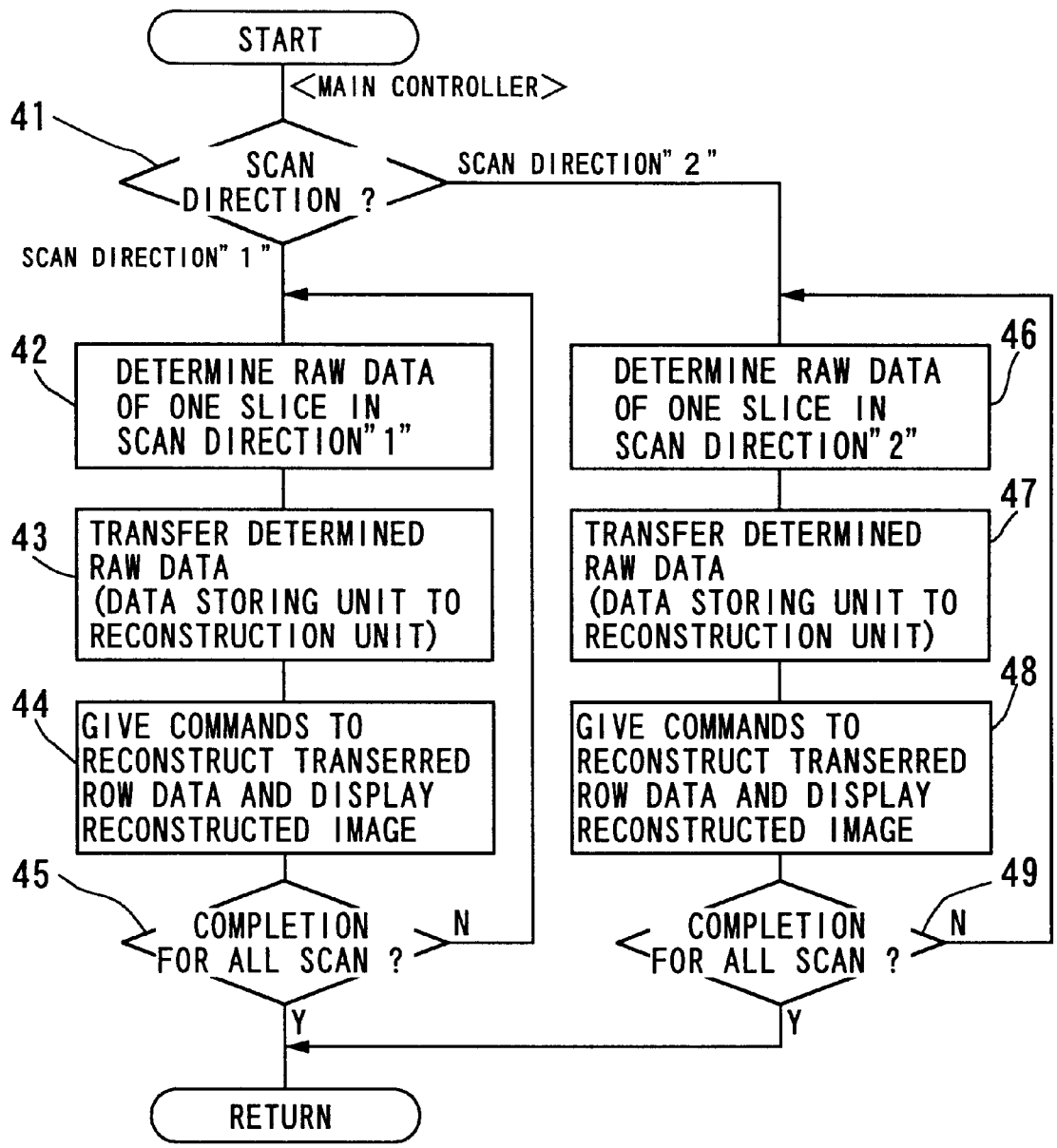
FIG. 7 shows a schematic flowchart for controlling the orders of reconstruction and display of images in compliance with each scan direction, which is executed by a main controller in a first embodiment.

In executing a predetermined main program (not shown), the main controller 30 executes at proper timing processing expressed by a flowchart shown by FIG. 7 in order to control the reconstruction order for tomographic images.

In processing of FIG. 7, the main controller 30 determines whether the scan direction is a scan direction "1" or "2", based on operational information given via the input device 39 (FIG. 7, step 41).

When this determined result is the scan direction "1", as in FIG. 5A, slices advancing (or consecutively positioning) in the slice direction "1" are determined one by one (step 42). Then raw data for one slice determined are read out form the data storing unit 35 to transfer them to the reconstruction unit 36 (step 43). The main controller 30 issues to the reconstruction unit 36 a command to reconstruct the transferred raw data, while it issues to the display 37 a command to display tomographic data reconstructed in the last interrupt, i.e., one frame before (step 44). Then it is determined that these processes have completed for all the slices of all the scans (step 45). If NO at this determination, the above steps 42 to 44 are repeated until the determination of YES comes out at step 45. YES at step 45 permits the main controller to return to the main program.

If the scan direction is recognized as the scan direction "2" at step 41, processing at steps 46 to 49 are executed in sequence. In this state, because the scan direction is "2" (refer to FIG. 5B), slices advancing in the slice direction "2" are determined one by one (step 46), raw data are read out slice by slice from the data storing unit 35 to transfer them to the reconstruction unit 36 (step 47), and reconstruction and display are commanded in the same way as above (step 48). The processing at these steps is repeatedly continued for all the slices (step 49).

Thus in the case of the scan direction "1", raw data are transferred to the reconstruction unit 36 slice by slice in the order of:

slices A1, A2, A3, A4, A5, B1, B2, B3, B4, B5, C1, C2, C3, C4, and C5, then reconstructed in this order. The reconstruction unit 36 produces one tomographic image per one time of reconstruction. The data of reconstructed tomographic images are then stored in the data storing unit 35, in addition to being automatically displayed as a tomographic image by the display processor 37 in sequence slice by slice, as shown in FIG. 8.

Figures 8, 9A, 9B:
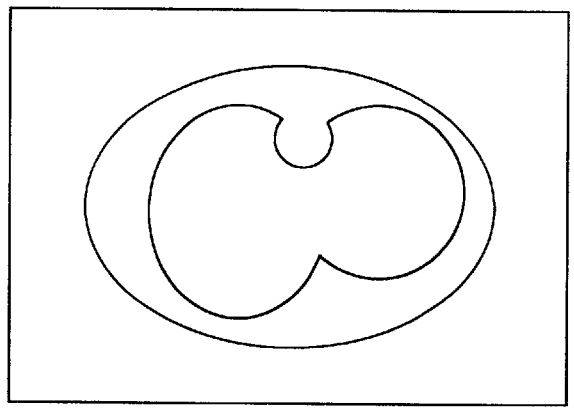
FIG. 8 exemplifies an image that is reconstructed and displayed one by one.
FIGS. 9A and 9B represent examples of timing between reconstruction and display in the first embodiment.

Since this image display is carried out after reconstruction, the relationship in timing between the reconstruction and the display becomes as shown in FIG. 9A, where the display is delayed by one frame and follows the reconstruction.

On one hand, in the case of the scan direction "2", raw data are transferred to the reconstruction unit 36 slice by slice in the order of:

slices C5, C4, C3, C2, C1, B5, B4, B3, B2, B1, A5, A4, A3, AZ, and A1, then reconstructed in this order. The data of reconstructed tomographic images are then stored in the data storing unit 35, in addition to being automatically displayed as a tomographic image by the display processor 37 in sequence slice by slice, as shown in FIG. 8. The relationship in timing between the reconstruction and the display becomes as shown in FIG. 9B, where the display is delayed by one frame and follows the reconstruction.

If the order to reconstruct and display images are set in a fixed manner as described in the prior art, sliced images are displayed differently from its scanning order at either of the scan direction "1" or "2", causing the displayed images being reversed from a scan position (or slice position) viewpoint. This reversed condition can be explained in the example of FIG. 5B, wherein the display order of images obtained in the scan direction "2" will be:

slices C1, C2, C3, C4, C5, B1, B2, B3, B4, B5, A1, A2, A3, A4, and A5.

As understood from this, for each scan, the slice C1 (or B1 or C1) which is the farthest from the frontal side is first displayed, and then the slices C2, C3, C4, and C5 (or B2, B3, B4, and B5 or A2, A3, A4, and A5) which gradually return to the frontal side are displayed in turn. In other words, images are displayed in the opposite order to a direction along which the scanning advances, giving an operator or interpreter a confused feeling. This leads to a difficult or cumbersome three-dimensional interpretation of images.

Figures 10A, 10B:
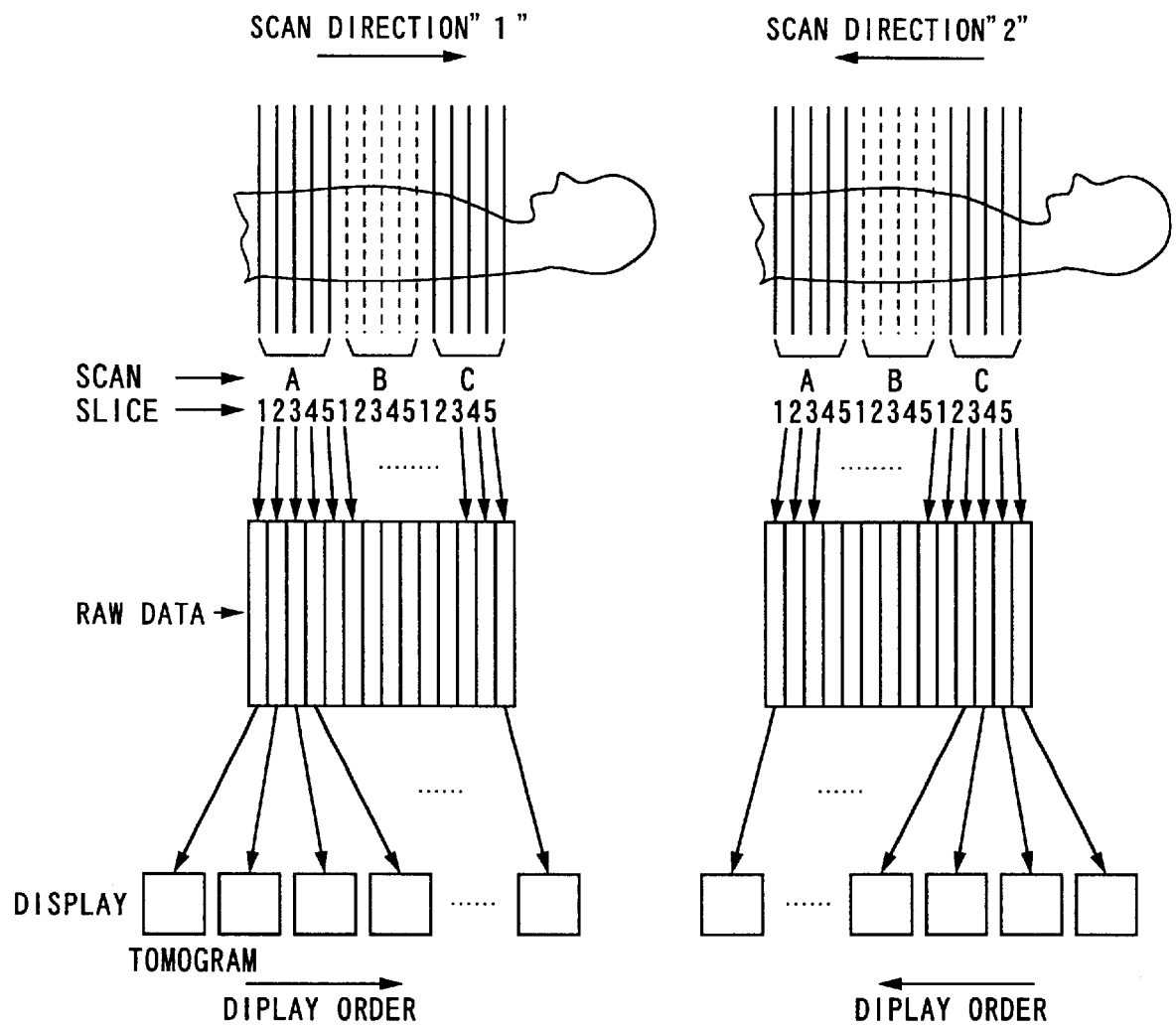
FIGS. 10A and 10B conceptually shows in each scan direction the relationship among the orders of scanning, the orders of reconstruction of raw data, and the orders of display of images.

However, in this embodiment, as shown in FIGS. 10A and 10B, for each scan direction "1" or "2", the slice positions of processed images constantly agree with a designated scan direction, along which the images are reconstructed and displayed in turn. This is also true when round-trip scanning which goes in the scan direction "1" and returns in the scan direction "2".

Therefore, an operator or interpreter can easily interpret images in their displayed order, excluding the foregoing confusion. This facilitates an accurate understanding of three-dimensional pathologic states within a scanned region, thereby increasing efficiency in diagnosis and remarkably relieving interpretation work.

Although in the first embodiment, raw data for reconstruction are transferred slice by slice from the data storing unit 35 to the reconstruction unit 36 under control of the main controller 30, the present invention is not restricted to this mode. As to this data transfer, a wide range of modifications are provided as below.

Modification (1-1)

For example, the main controller 30 is constructed such that it determines the reconstruction order of slices in conformity with the scan direction and informs the reconstruction unit 36 of information about determined slice positions. The reconstruction unit 36 is designed so that it reads raw data for a specified slice from the data storing unit 35 for reconstruction. Such construction allows the reconstruction unit 36 to share transfer processing o:r raw data which was partly operated by the main controller 30 in the first embodiment, reducing the calculation load of the main controller 30.

Modification (1-2)

Further an amount of raw data transferred from the data storing unit 35 to the reconstruction unit 36 can be modified. For example, the main controller 30 can be operated to batch-transfer them for one scan (for example, five slices: a plurality of slices) at once, not for only one slice. In this case, the reconstruction unit 36 is configured to select raw data for each slice from all the raw data batch-transferred for one scan, under control of the main controller 30, and reconstruct the selected raw data. Consequently it is not necessary for the main controller 35, in itself, to be involved directly in selection of raw data. This also relieves a burden on the main controller 35.

Modification (1-3)

There is still provided a technique that previously controls a data format in accord with a desired scan direction in storing raw data into the data storing unit 35.

Figures 11A, 11B:
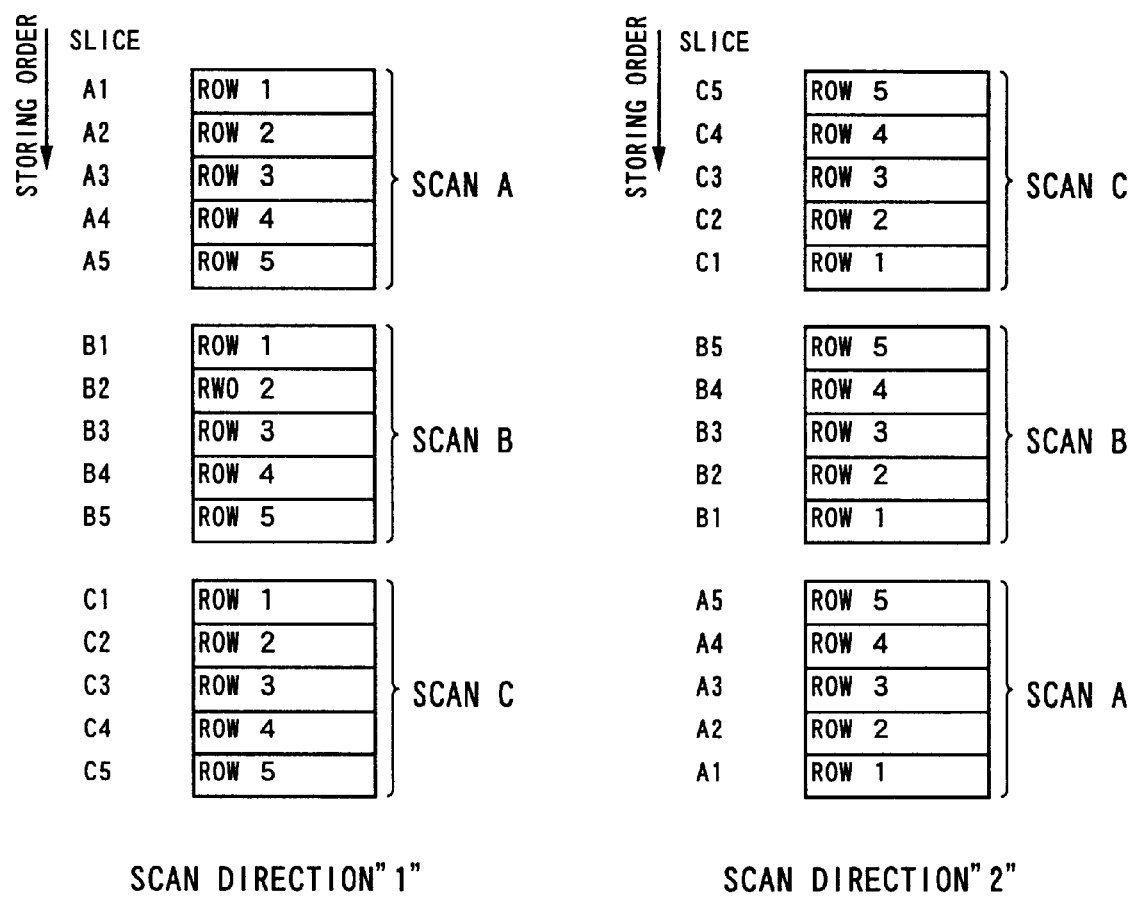

For instance, as shown in FIG. 11A, raw data are stored at addresses in the unit 35, the addresses corresponding to the order (A1, A2, A3, ... ) along which the scans A, B, and C advance in the foregoing scan direction "1" (refer to FIG. 5A). Also, as shown in FIG. 11B, raw data are stored at addresses in the unit 35, the addresses corresponding to the order (C5, C4, C3, ... ) along which the scans C, B, and A advance in the forgoing scan direction "2" (refer to FIG. 5B).

This control of the data format can be performed by the DAS 24 or correction unit 34. Specifically, the DAS 24 changes an output order of raw data (acquisition data) according to the scan direction "1" or "2", or, the correction unit 34 changes an output order of corrected raw data according to the scan direction "1" or "2". Alternatively the data storing unit 35 is able to re-map data once stored into the data format shown in FIG. 11A or 11B.

It is thus enough that the main controller 30 gives both the data storing unit 35 and the reconstruction unit 36 a data-transferring command always having the same format, independently of any scan direction. Additionally the reconstruction unit 36 can reconstruct on a predetermined constant procedure independent of any scan direction. It is possible to perform data transfer and reconstruction without particular attention paid to the scan directions; nevertheless, the tomographic images are displayed based on an order reflecting differences in the scan directions. Thus the calculation load of the main controller 30 can be lowered, while the reconstruction unit 36 can perform reconstruction in an automatic fashion, because it only reconstruct raw data in an order along which they have been received. As a whole, control and processing concerning the raw data transfer and reconstruction is noticeably simplified.

Second Embodiment

Figure 12:
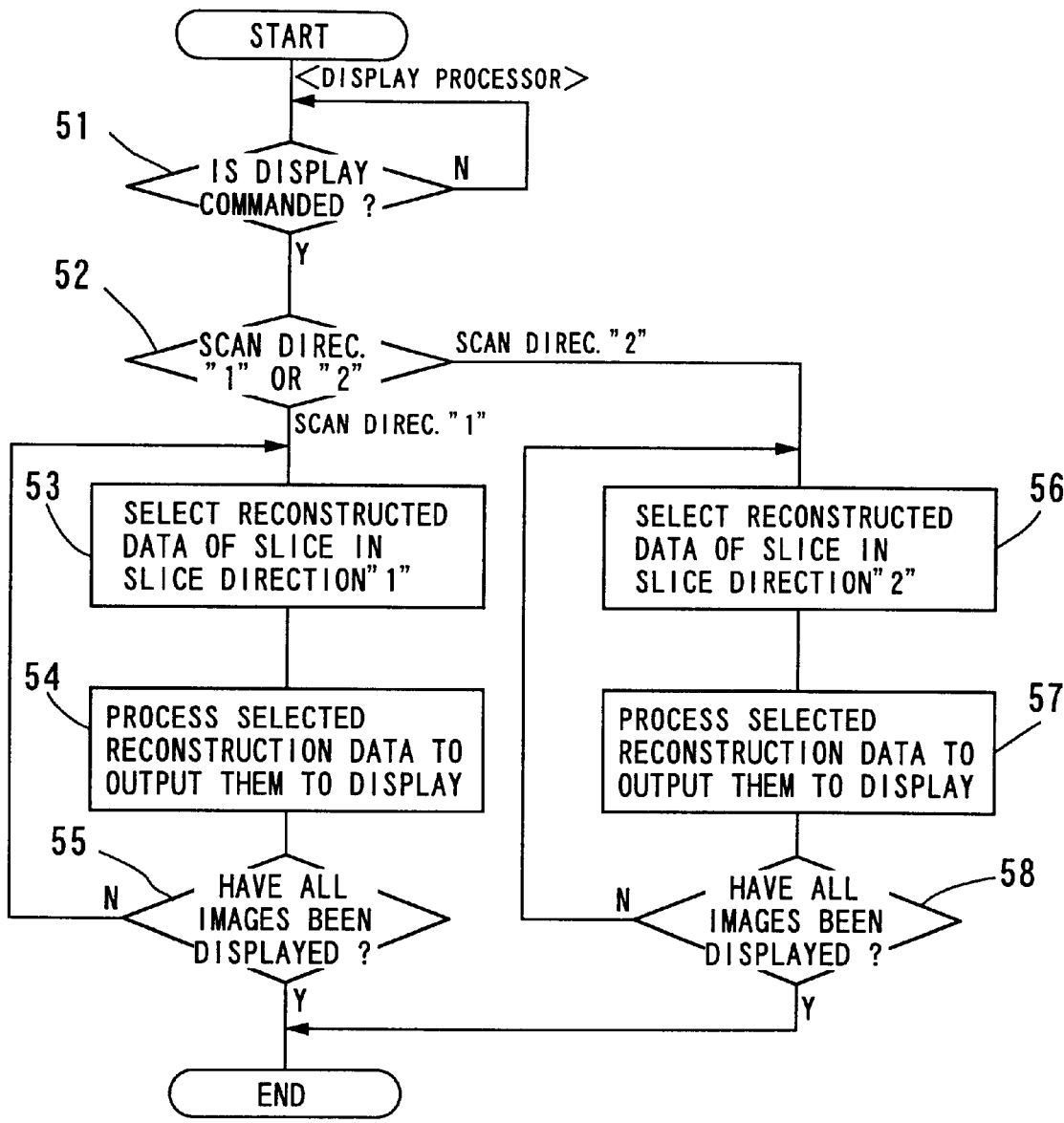
FIG. 12 is a schematic flowchart for controlling the order to display images, which is executed every scan direction by the main controller in a second embodiment.

Referring to FIGS. 12 and 13, a second embodiment of the present invention will be described.

A feature about an X-ray CT scanner as a diagnostic is that a display order of images reconstructed is solely controlled according to differences in the scan direction, and images are one by one displayed on a display in this display order.

The hardware configuration of the X-ray CT scanner is identical to that described in the first embodiment. Under control of the main controller 30, the reconstruction unit 36 reconstructs a plurality of images from raw data of a plurality of slices acquired by each one scan, which have been received from the data storing unit 35, within an interval of one frame or a certain interval. Data of a plurality of reconstructed tomographic images for each scan are stored in the data storing unit 35 and transferred to the display processor 37, responsively to a command from the main controller 30.

The display processor 37 temporarily stores the received image data for each scan into an inner memory thereof for processing shown in FIG. 12.

In the processing of FIG. 12, the display processor 37 determines an image display command given by the main controller 30 (step 51), and determines either scan direction from operational information or others (step 52). If the scan direction "1" shown in FIG. 5A is determined, steps 53 to 56 are processed, whereas if the scan direction "2" shown in FIG. 5B is determined, steps 56 to 58 are processed.

For the scan direction "1", reconstructed image data are selected in a slice position order along the scan direction "1" (step 53), necessary processing is performed with the selected data for display (step 54). Such processing is repeated scan by scan for all the reconstructed image data.

Figure 13A:
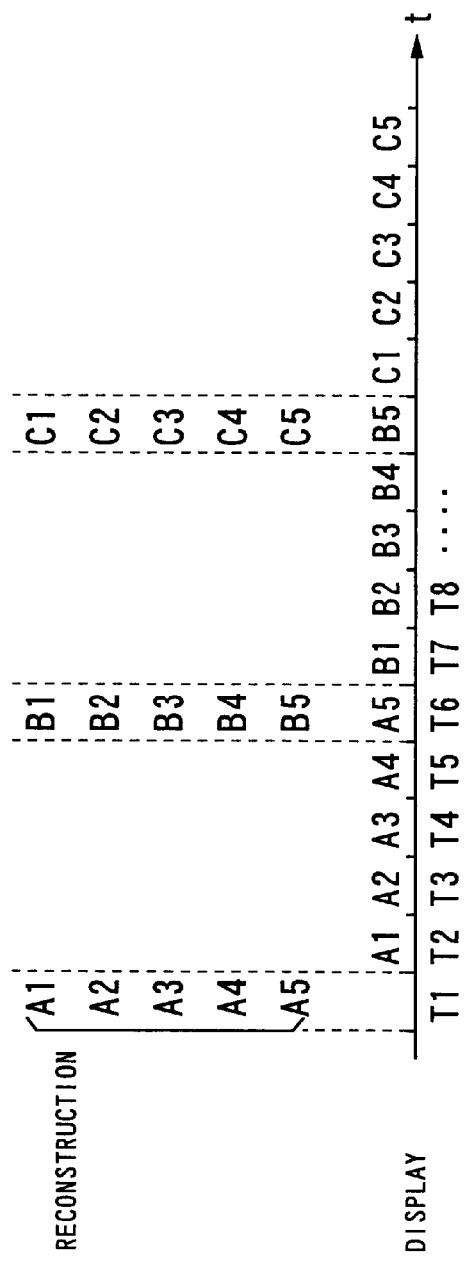
FIGS. 13A and 13B represent examples of timing between reconstruction and display for each scan direction in the second embodiment.

One example of timing of reconstruction and display based on the above processing is shown in FIG. 13A. Five images for a first scan A are reconstructed in a frame interval T1, then images of slices A1, A2, A3, ... , A5 are displayed in turn during the succeeding five frame intervals T2, T3, ... , A6, as shown in FIG. 8. In the frame interval T6 in which the image of the last slice A5 is displayed, the batch-reconstruction for the next scan B is carried out. Like the above, such batch-reconstruction and sequential display continue.

Figure 13B:
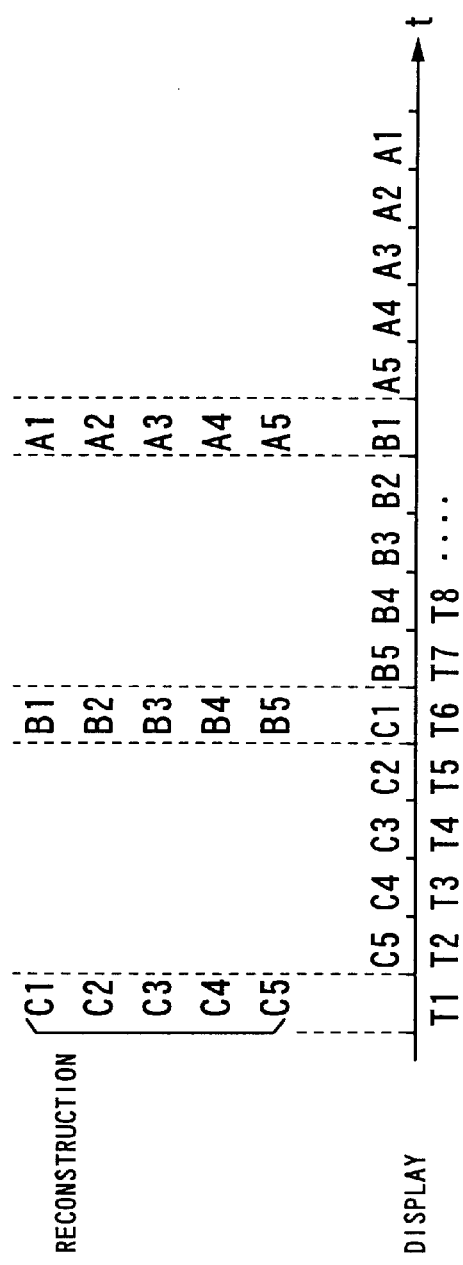

In the case of the scan direction "2", reconstructed image data are selected according to a slice position order along the scan direction "2" and displayed on the principle above-mentioned (steps 56 to 58). One such example is shown in FIG. 13B in terms of timing of reconstruction and display. Because the scan direction "2" is the opposite of the scan direction "1" the slices are subjected to be displayed according to this direction "2".

In the processing executed by the display processor 37, reconstructed image data can be stored again in the data storing unit 35, with the stored data being subjected to the foregoing processing by the display processor 37. Namely, from the data for a plurality of frames of images again stored in the data storing unit 35, slices are selected in an order in either slice direction "1" or "2", then their slice images are displayed in sequence. This display can reduce a necessary storage capacity of a frame memory incorporated in the display processor 37.

In the X-ray CT scanner of the second embodiment, a plurality of images acquired by a multi-scan are displayed in a slice position order along a desired scan direction. Therefore, no matter how the scan direction may be specified, a situation that images are reversely displayed in the scan direction is steadily avoided. Therefore the identical advantages to those in the first embodiment can be obtained.

Third Embodiment

Figure 14:
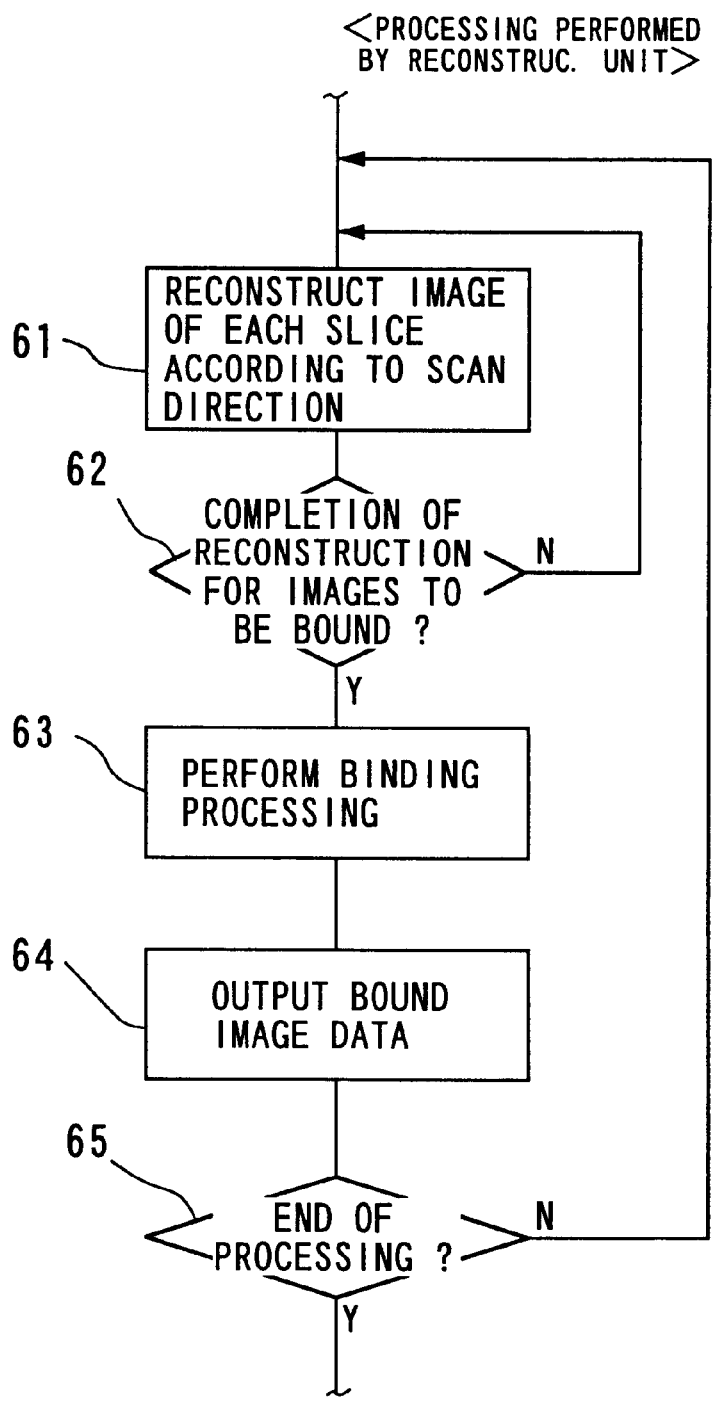
FIG. 14 is part of a schematic flowchart for performing binding processing of slices as well as control of the order of image display according to each scan direction, which is executed by the main controller in a third embodiment.

Referring to FIGS. 14 and 15, an X-ray CT scanner of a third embodiment will now be described.

In order to control a slice thickness, known is an X-ray CT scanner that performs processing, referred to as "binding processing", as published by an examined Japanese Patent Publication No. 63-62215. The binding processing is a technique for binding image data of two or more contiguous slices. In reality, the binding is carried out by adding or averaging pixel values of plural images to each other. Thus, the binding is sometimes expressed by another term "addition or synthesis". In this embodiment, this binding is combined with one feature of the present invention, that is, the finally displayed order of slice images controlled according to a specified scan direction.

The hardware configuration is, in itself, identical to that already described. But, as concerning software operation, the reconstruction unit 36 is constructed to perform partial processing shown in FIG. 14, as part of the entire processing assigned thereto.

Specifically, using raw data received every slice or scan from the data storing unit 35, the reconstruction unit 36 reconstructs raw data of each slice in the slice position order along a specified scan direction for temporary storage of the reconstructed tomographic image data (step 61). Namely image date of one slice is reconstructed every process of reconstruction.

Then the unit 36 determines whether or not reconstruction has been completed for a desired amount of slices of which images are used for binding processing (step 62). One example is two in slices which is to be bound, which will be explained below. Thus, on completing the reconstruction for the first and second slices contiguous to each other, the determination at step 62 becomes affirmative, proceeding to step 63. At this step, the binding is performed with the two-slice reconstructed image data. Practically the pixel values are averaged pixel by pixel between the two image frames, producing one image of one bound slice. By way of example, if each slice multi-scanned is 2 mm in thickness, an image of a slice having a thickness of 4 mm is produced on calculation by binding.

Image data thus-bound are sent, as image data of one slice, from the reconstruction unit 36 to both the data storing unit 35 and the display processor 37 (step 64). The data of a bound image are not only stored in the unit 35 but also subjected to necessary processing by the display processor 37 for visualization on the display 38, on which an image is displayed one by one as exemplified in FIG. 8.

The processing at steps 61 to 64 is repeated until the binding and display are completed for all the slices (step 65). As a result, bound tomographic images are presented in turn on the display 38 at intervals.

Figure 15A:
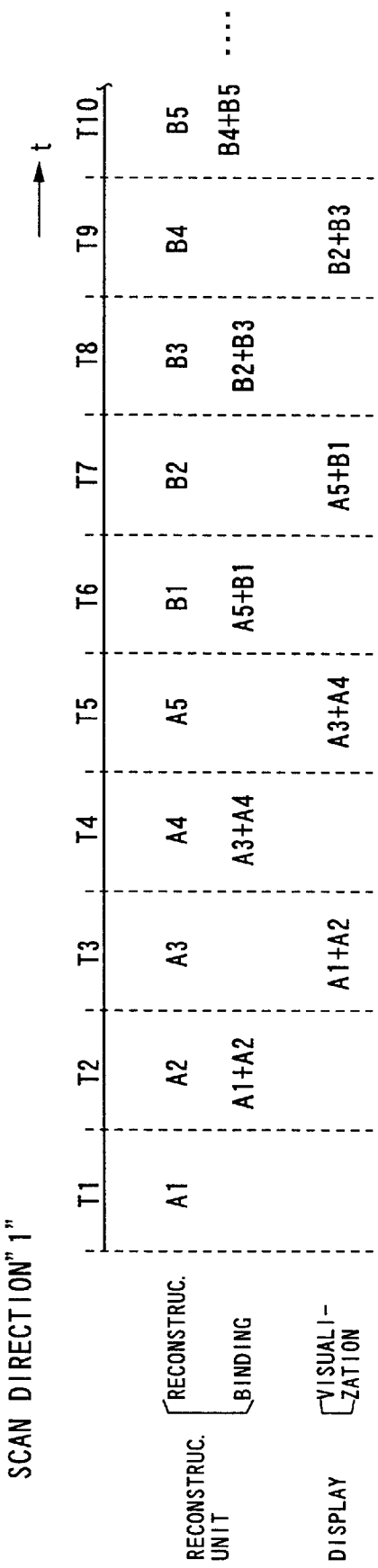
FIGS. 15A and 15B are illustrations showing timing among reconstruction, binding processing, and display for each scan direction in the third embodiment.
Figure 15B:
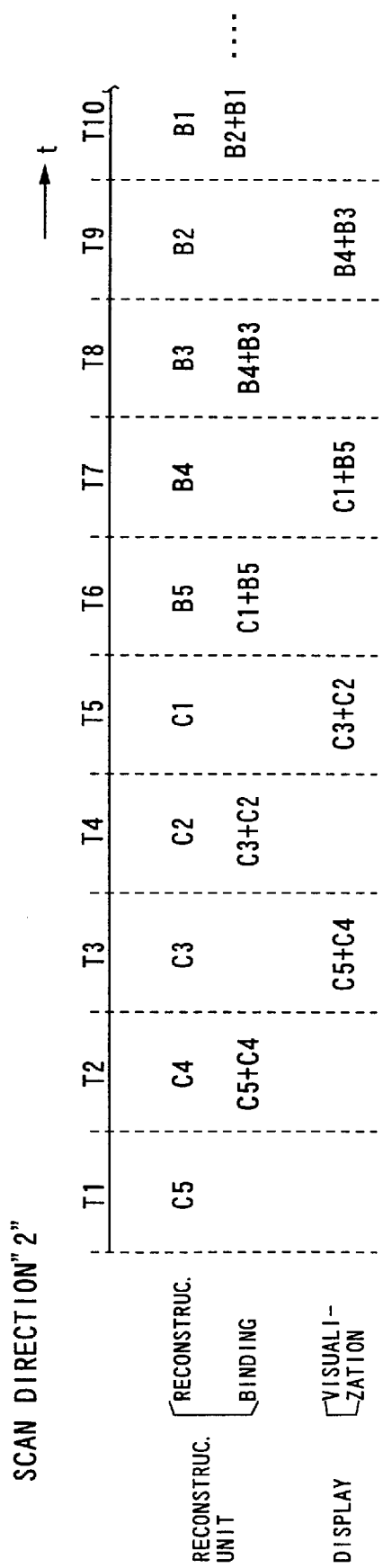

One such example is shown every scan direction in FIGS. 15A and 15B in timing of reconstruction, binding, and display. This example shows that the number of binding slices is two. In the case of the scan direction "1" (refer to FIG. 5A), on completion of reconstruction for two slices A1 and A2, for example, binding "A1+A2" is performed, and then displayed in the next frame interval T3. The bound images is displayed in each frame interval thereafter. Like the above, in the scan direction "2", reconstruction, binding, and display are performed on the same principle, but along the opposite scan direction "2".

Therefore, the display order control in binding a plurality of images is still effective, the bound images being displayed in an display order of slices advancing along a specified scan direction. The same or identical advantages as or to those described before can be provided.

As to this third embodiment, a variety of modifications are provided.

Modification (3-1)

First, the number of slice images bound is not confined to two. Three or more slice images are available. Thus, a total slice thickness (bound thickness) can be changed.

Modification (3-2)

In the third embodiment, each of a plurality of slices is independently reconstructed, before the reconstructed image data are averaged (bound). Alternatively, as-acquired raw data for a plurality of slices can be averaged (bound) before reconstruction. The averaged raw data of one frame are then subjected to reconstruction, also producing a bound tomographic image.

Modification (3-3)

The foregoing binding processing and display can be combined with the reconstruction technique described in the second embodiment.

To be specific, the reconstruction unit 36 reconstructs at once a plurality of slice images per one scan, as batch processing or processing lasting in a certain period. The binding of images starts from the next frame interval, according to a specified scan direction. One such example is shown in FIGS. 16A and 16B which show timing charts representing the operation of reconstruction, binding, and display.

This modification also provides valuable advantages comparable to the forgoing embodiments and modifications.

The following are embodiments applicable to the forgoing embodiments and modifications.

Fourth Embodiment

Figure 17:
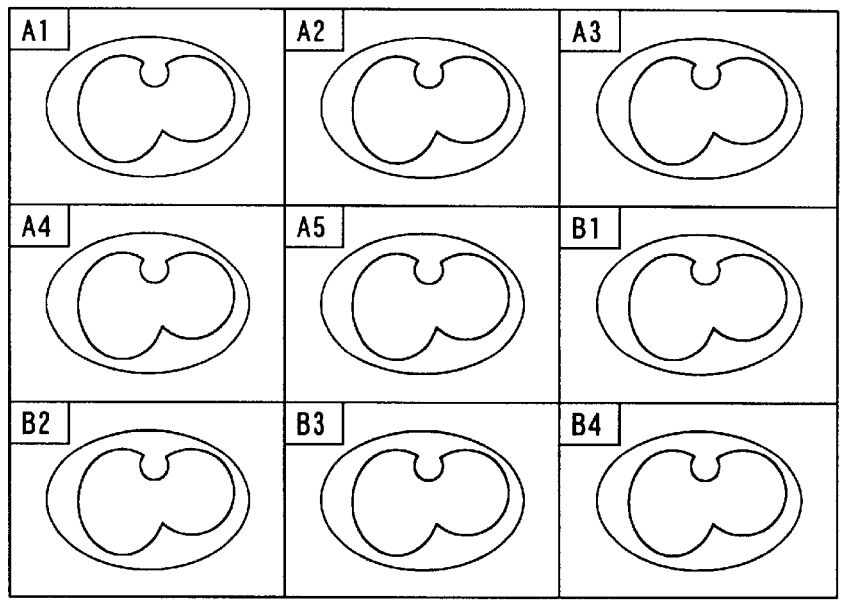
FIG. 17 shows one example of images displayed in a fourth embodiment of the present invention.

A fourth embodiment relates to a display mode of images obtained from a minimum of four slices by the multi-scan (i.e., two or more scans for two or more slices per scan). Specifically, the display mode is that a plurality of images obtained by the multi-scan are all list-displayed on the same screen, as shown in FIG. 17.

To this list display, the display processor 37 is designed to comply with the following procedures. When receiving a command to list-display images from the main controller 30, the display processor 37 waits until it receives all reconstructed image data to be list-displayed by transfer (or waits until all reconstructed image data are stored in the data storing unit 35), forms a frame of image data in which a plurality of frames of accepted image data (or stored) are arranged in a divided fashion, perform necessary processing with the formed image data, and send them to the display 38.

Accordingly, on the display 38 is list-displayed a minimum of four slice images. Observing these images enables a steady understanding of three-dimensional, internal structures in a region to be diagnosed, like FIG. 8 wherein the images are updated consecutively. Further, this list-display of images permits an interpreter to comparatively observe images in an easy-to-operate manner, on account of all the images displayed at a time.

Fifth Embodiment

A fifth embodiment relates to a reconstruction method.

Although not described in the above embodiments and their modifications, the invention is independent of reconstruction methods of images. Reconstruction methods applicable to the system of the present invention are enough if they can reconstruct an image of each slice for each scan in performing the multi-scan. One preferred example is a "Feldkamp reconstruction method" proposed by Feldkamp. The Feldkamp reconstruction method is a calculation way that considers the irradiation angles of X-ray beams to the rotation axis direction of a gantry and reconstruct acquired data by means of backprojection in accord with their acquisition paths.

Accordingly there can be provided CT scanners that obtain as many as images at a time, raising the scan speed. Because a proper reconstruction method according to scan conditions can be selected, degrees of freedom for imaging is also increased.

A Sixth Embodiment

A sixth embodiment is concerned with tilting the gantry. The gantry can be tilted such that the plane passing the X-ray beam center in the slice direction becomes oblique to the tabletop 2a. This is useful when obtaining raw data of a plurality of oblique slices to the body axis of a patient. These raw data are, for example, reconstructed and formed into bound images.

In this case, independently of any scan direction, slice images are displayed according to a scan direction along which a multi-scan advances, providing the identical advantages to those described before.

Seventh Embodiment

A seventh embodiment relates to another example of the scan direction.

Scanning is not always limited to one way of the scan direction "1" or "2" Scanning can be repeated along the scan direction "1" or "2" a plurality of times. Further scanning can be performed a round-trip direction first going along the scan direction "1", then returning along the scan direction "2".

Figure 18:
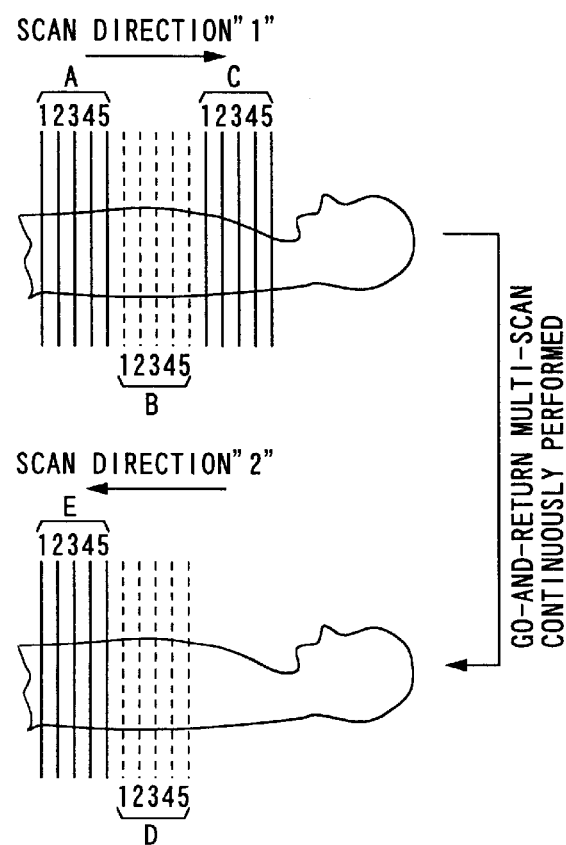
FIG. 18 is an illustration of scan positions in a multi-scan which goes forward and returns restlessly, which is adopted in a seventh embodiment of the present invention.

According to the seventh embodiment, as shown in FIG. 18, scanning is performed in a round-trip scan direction first advancing in the direction "1" with three scans A, B and C, then continuously returning in the direction "2" with two scans D and E. This scanning can also be done under control of the main controller 30.

Figure 19:
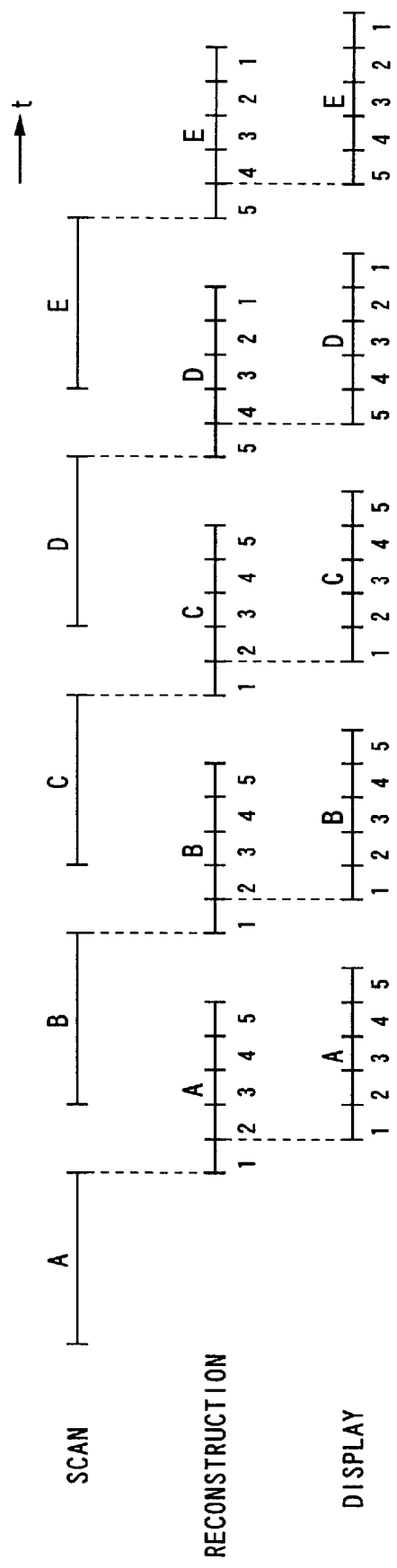
FIG. 19 represents timing chart among scans, reconstruction, and display executed based on the scanning in FIG. 18.

For this multi-scan, timing among the scans A to E, reconstruction, and display is exemplified by FIG. 19. When the scan directions have been changed from its "1" to "2", the main controller 30 controls the orders of raw data transferred from the data storing unit 35 to the reconstruction unit 36, so that the order to reconstruct and display images is altered into the opposite way of "D5, D4, D3, . . . ". Even if the scan directions change by returning, the order of reconstruction and display is also changed in agreement with a changed scan direction. Therefore, like the foregoing embodiments and modifications, easy-to-observe, three-dimensionally understandable images are provided.

Eighth Embodiment

An eighth embodiment relates to a modification of the scan direction and a image display mode.

Figure 20:
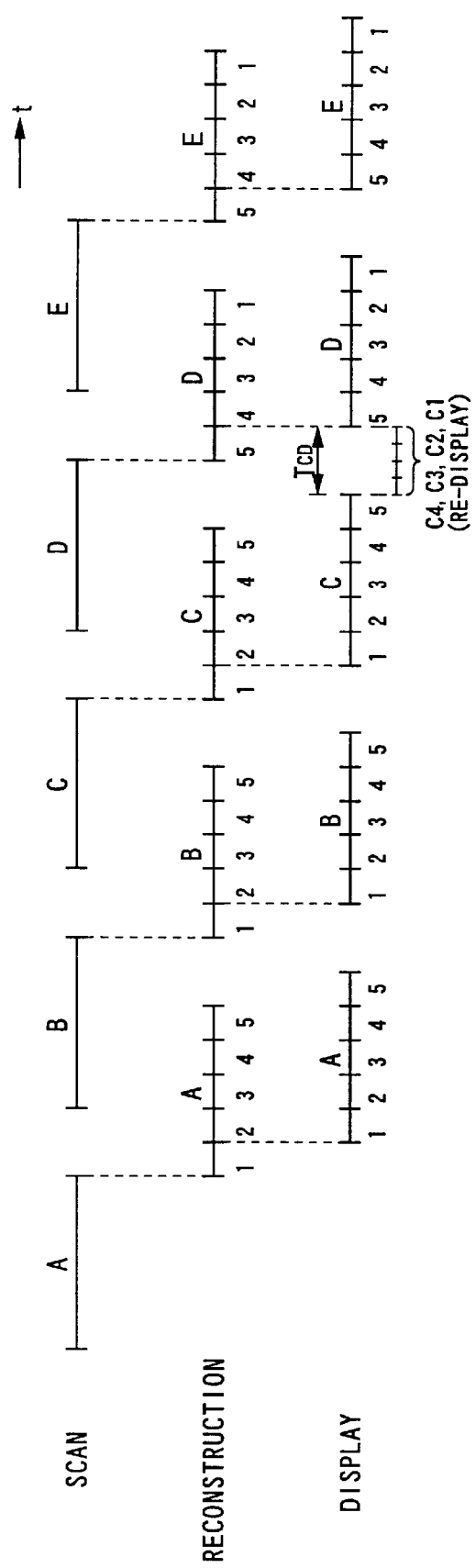
FIG. 20 represents timing chart among scans, reconstruction, and display executed based on the scanning in FIG. 18 in an eighth embodiment of present invention.

Like the seventh embodiment, when the scan direction is reversed in a round-trip multi-scan, it is preferred that images acquired by a scan performed immediately before the reverse are re-displayed during an interval of the reverse. This is exemplified in FIG. 20. When the scanning makes transition from the scan C to D, four images of slices C4, C3, C2, and C1 which have already been reconstructed and displayed are again displayed (re-displayed) in this order during an interval $T_{CD}$ between the scans C and D.

The re-display is carried out, for example, by the display processor 37. On receiving a command to notify the interval $T_{CD}$ from the main controller 30, the display processor 37 reads those image data from the data storing unit 35 for re-display. After completing the re-display, the scans D and E are performed in the reversed scan direction "2" as described before.

Such re-display of part of images in the reverse of the scan directions keeps continuity in slices to be displayed, such as ". . . , C4, C5, C4, C3, C2, C1, D5, D4, . . . " In other words, a situation that slices to be displayed jumps from C5 to D5 is suitably avoided, preventing observers from having a feeling of discontinuity in slices to be displayed. Thus image observation can easily be performed in a stable manner.

Ninth Embodiment

A ninth embodiment relates to a region to be scanned.

Figure 21:
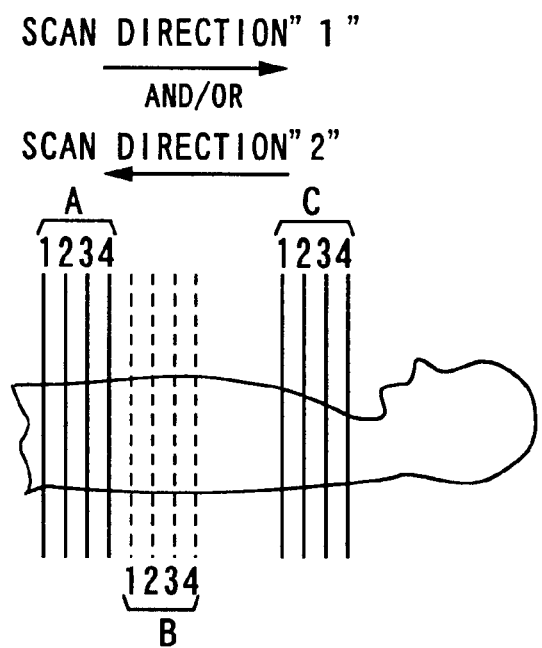
FIG. 21 shows scan positions according to a ninth embodiment of the present invention.

A region to be scanned applicable to the present invention is not necessarily restricted to a single region continuous in the slice direction. For example, as shown in FIG. 21, two separate regions can be employed which consist of one region to which scans A and B are applied and the other, spatially separated from the one region, to which a scan C is applied, both of which are scanned in the scan directions "1" and/or "2". Such a plurality of regions can be scanned, under control of the main controller 30, by such control as X-ray irradiation, rotation of the X-ray tube and detector, and tabletop movement, which is accomplished by the cooperative operation among the high-voltage controller 31, couch controller 32, and gantry controller 33.

All the foregoing display-order control and others can be applied to this scanning of discontinuous plural regions.

Tenth Embodiment

A tenth embodiment is concerned with medical imaging modalities other than an X-ray CT scanner.

A diagnostic system according to the present invention only requires that scanning is performed a plurality of times to acquire data of a plurality of images of which slice positions differ from each other, each time the scanning being performed at a changed new position. It is enough that means for controlling the order to produce images or to display images according to a desired scan direction are installed in such diagnostic system.

In a field of medical imaging modalities, other than X-ray CT scanners, there are provided CT scanners using radiation except X-rays, MRI (magnetic resonance imaging) systems, and nuclear medicine diagnostic systems. If required, industrial CT systems can adopt the present invention.

Figure 22:
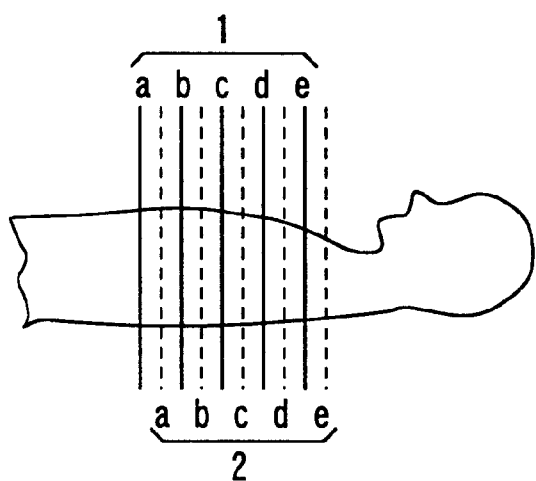
FIG. 22 shows scan positions realized by an MRI system, which is a tenth embodiment of the present invention.

By way of example, FIG. 22 shows slice positions performed by an MRI system. In MRI, for faster echo data acquisition, known is an imaging technique that one volume region is subjected to data acquisition divided into two times of scanning, as shown therein. The first scanning is performed for echo data acquisition of slices 1a to 1e, and the next scanning is for slices 2a to 2e. Each of the slices 1a to 1e and each of the slices 2a to 2e are selectively spin-excited so that they are arranged alternately and contiguously (or adjacently). By the configuration of the present invention installed in the MRI system, a slice position order to reconstruct or display images are set, by way of example, to "1a, 2a, 1b, 2b, . . . , 1e, 2e." Like this, scanning may be performed with one region three or more times. Alternatively, such slice position order can be set to "2e, 1e, 2d, 1d, . . . , 2a, 1a."

Therefore, like the case of the foregoing X-ray CT scanner, a plurality of images are displayed in a constant order in a specified scan direction. This makes the observation of images easier.

Eleventh Embodiment

An eleventh embodiment is concerned with display of information about the reconstruction order or display order set by the foregoing various embodiments and modifications. In this embodiment, such order information is displayed on the display 38 serving as the nearest console screen. This display is done by the main controller 30 to send a display command to the display processor 37.

For example, the slice positions (corresponding to such order information) shown in FIG. 5A or 5B are visualized in a proper display mode on the display screen. This display allows an operator who is in scan plan to visually understand the slice positions and the order to display them. The alteration can be done instantly there.

Twelfth Embodiment

Referring to FIGS. 23 to 26, a twelfth embodiment of the present invention will now be described, where the diagnostic system is realized by a multi-slice type of X-ray CT scanner configured in FIGS. 2 to 5.

In the forgoing various X-ray CT scanners, the reconstruction order or the display order is automatically set in agreement with a scan direction after it has been specified once, but a manual intervention is far from the setting.

To improve such inconvenience, the X-ray CT scanner of this embodiment allows an operator to manually set the reconstruction order or display order and visually display information about the set order on the display 38 prior to scanning. In addition to providing an operator or interpreter tomographic images that does not pose a mixed feeling, but produce spatially easy-to-understand images, choices in setting the orders can be enriched and the slice positions can easily be confirmed in advance.

Figure 23:
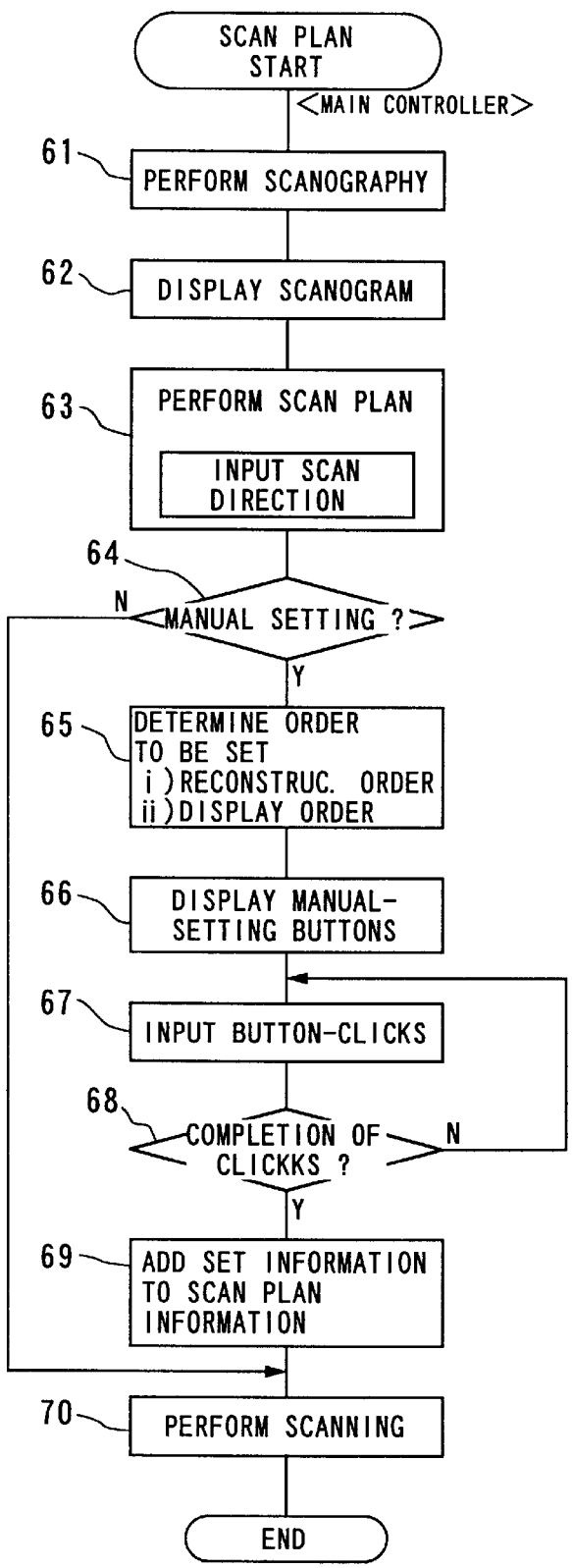
FIG. 23 is a schematic flowchart showing processing executed by the main controller in accordance with a twelfth embodiment of the present invention.
Figure 24:
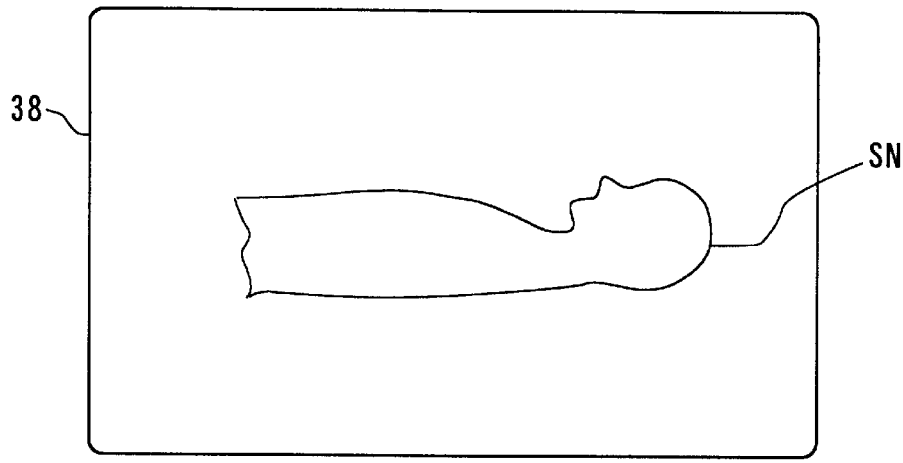
FIG. 24 is a scan plan image for explaining manual setting of the order of display in the twelfth embodiment.

To achieve this, the main controller 30 executes the processing shown by an outlined flowchart in FIG. 23. First, the main controller 30 instructs relevant units to acquire data of a scanogram of a patient P (step 61). Then proceeding to step 62, the main controller 30 commands the display processor 37 to display the scanogram data. Accordingly, a scanogram SN is presented on the display 38, as shown in FIG. 24.

Figure 25:
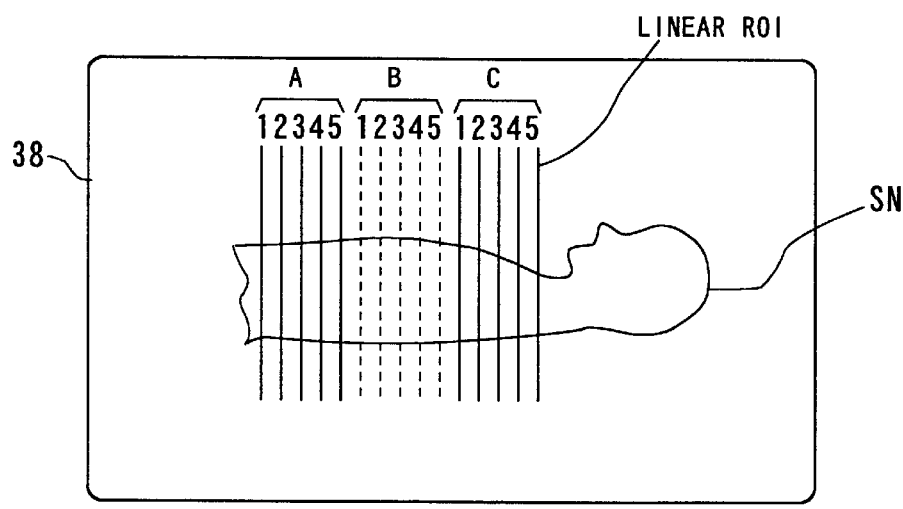
FIG. 25 is a scan plan image for explaining manual setting of the order of display in the twelfth embodiment.

Then, proceeding to step 63, the main controller 30 handles scan plan with an operator in an interactive manner. In this scan plan, multi-scan-related scan information including the number of scans, the number of slices per scan, scan positions, a slice thickness, a tube current amount, and a tube voltage amount are given by an operator. Responsively to this setting of the scan information, the main controller 30 places linear ROIs to shown all the slice positions for each scan on the displayed scanogram, as shown in FIG. 25, so that the positions to be sliced by the specified multi-scan method are visually shown. In the course of this scan plan, the main controller 30 reads and memorizes operator-specified information about a desired scan direction (i.e., scan direction "1" or "2" as shown in FIG. 5A or 5B).

After this, based on commands from the operator, the main controller 30 determines if the reconstruction or display order is manually set (step 64). If this determination is NO (i.e., automatic setting), the steps 65 and thereafter are skipped, directly proceeding to performing scanning (step 70). In this case of automatic setting, the reconstruction or display order is controlled by the techniques described the forgoing embodiments and modifications.

If YES at step 64 (i.e., manual setting), the steps 65 to 69 are processed in turn. At step 65, it is determined whether the order to be manually set is the reconstruction order (namely, order to reconstruct and display images) or the display order, base on button-clicked information by the operator.

Then the main controller 30 issues a command to the display processor 37 for display of manually setting a button BT at every slice position. As a result, as shown in FIG. 26, displayed on the screen of the display 38 are manually setting buttons BT each positionally corresponding to each slice, under the linear ROIs showing slice positions 1 to 5 for each of the three scans A to C.

Then, at steps 67 and 68, the main controller 30 reads clicked information generated by the operator who clicks any button BT and determines the completion of the clicking. By clicking operation with a mouse or others, as to either the reconstruction or display order, slice positions desired by the operator are recognized. The order is set according to the scan direction already specified.

Figure 26:
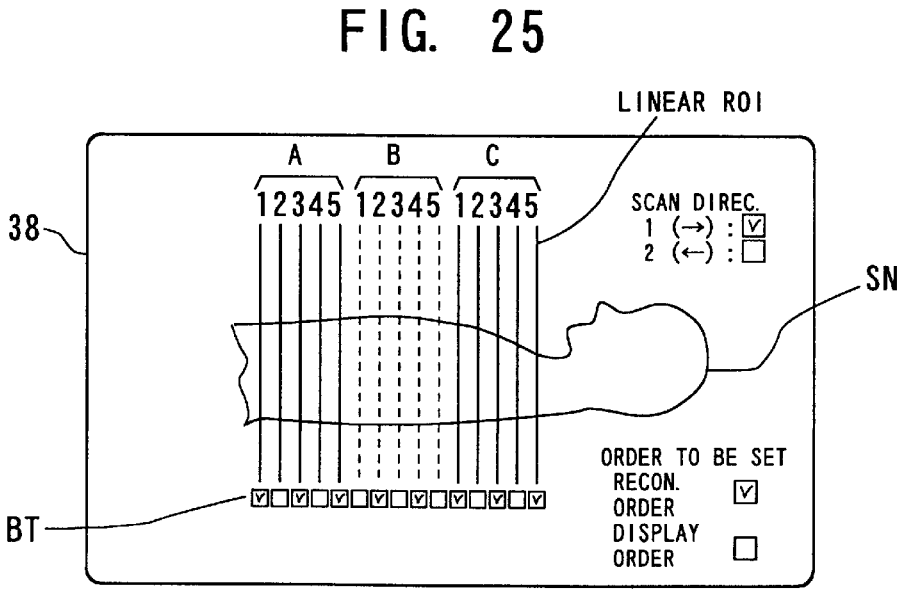
FIG. 26 is a scan plan image for explaining manual setting of the order of display in the twelfth embodiment.

For example, as shown in FIG. 26, in the case of the scan direction="1", the order=reconstruction order, and the clicked positions=every other button, the order of slices to be reconstructed and displayed are "A1, A3, A5, B2, B4, C1, C3, and C5". In this example, the scanning is performed with all the twenty-five slices, and raw data of each slice acquired. But actually reconstructed slices for display are every other one. Therefore all the raw data are once stored in the data storing unit 35 for later use. An alternative example is every three slices, every six slices, or others. In FIG. 26 configuration, instead of scanning on the scan direction "1" or "2", a round-trip multi-scan in the scan directions "1" and "2" is also available.

Then at step 69, the main controller 30 adds the order information manually set into the scan plan information. And based on it, scanning which complies with any of the forgoing embodiments or modifications is performed at step 70.

Accordingly, the reconstruction or display order as part of scan panning can be manually set into any order. When overviewing an entire region to be diagnosed and absolutely not requiring all images, the order can be manually set at regular or irregular slice intervals, providing an instant and convenient display manner. Additionally, for interpretation in detail, the raw data of all the slices which had been stored in the data storing unit 35 can be read out, reconstructed and displayed at any time.

Thus a combination of the manual setting and the automatic setting described before is effective in increasing choices of setting the order.

Further, the order information itself is visualized on the display, or monitor, installed in the control cabinet, or console, in the course of scan planning. An operator can visually confirm the order, facilitating understanding a spatial relationship among a plurality of slices in interpretation conducted in parallel with imaging. The orders can be changed easily there.

Concerning with the above manual setting, various modifications are provided as below.

Modification (11-1)

This modification relates to an easier technique for specifying slice positions.

Figure 27:
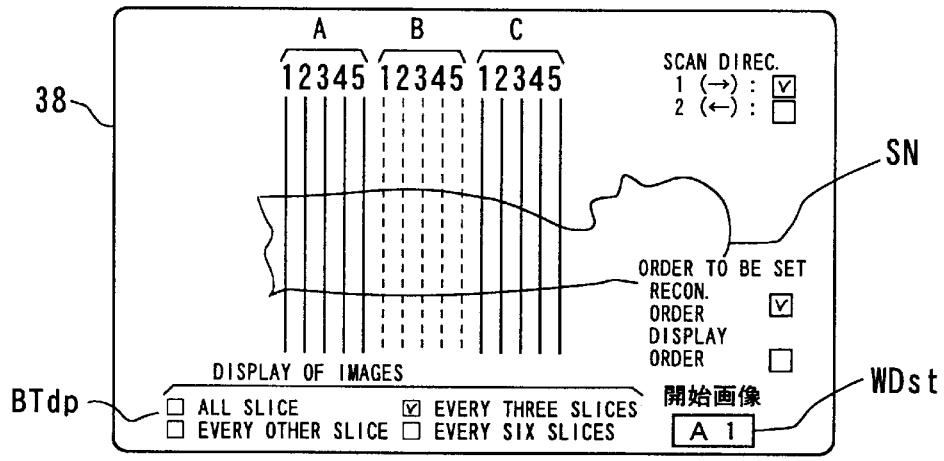
FIG. 27 is a scan plan image for explaining manual setting of the order of display in a first modification of the twelfth embodiment.

In place of selective specification for each of all the slice positions in a plurality of times of scans, there is provided an easy-to-specify technique, as shown in FIG. 27. In the figure, displayed on the display 38 are a window WDst for specifying an image to be displayed at first, and buttons BTdp for specifying slice positions to be displayed. As the later specification, choices prepared are, by way of example, "all slices", "every other slice", "every three slices", and "every six slices".

Thus, in scan plan, the type of order to be manually set (reconstruction or display order) and the scan direction (direction "1" or "2") are set as described before. Corresponding to steps 66 to 68 in FIG. 23, a slice position to be first displayed is specified into the window WDst with a keyboard or others, and slice positions of which images are displayed are specified by clicking any button BTdp with a mouse or others, thus the display order of images being automatically determined. Therefore, from all the slices scanned, raw data of desired slices are selected, reconstructed and displayed in the specified order or they are displayed in the specified order right after their batch reconstruction.

According to this modification, manual labor for setting slice positions for display is only two times for the window WDst and BTdp, simplifying the operation compared to the above embodiment.

Modification (11-2)

This modification exemplifies a specification technique of arbitrary slice positions to be displayed.

Figure 28:
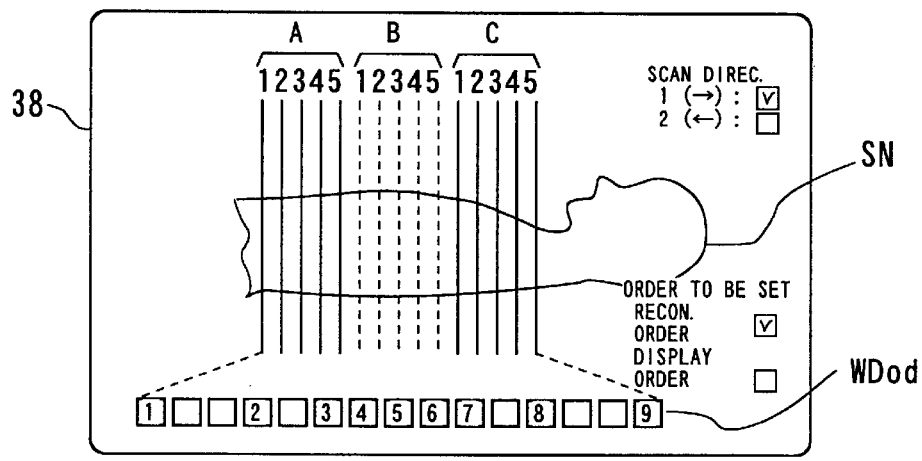
FIG. 28 is a scan plan image for explaining manual setting of the order of display in a second modification of the twelfth embodiment.
Figure 29:
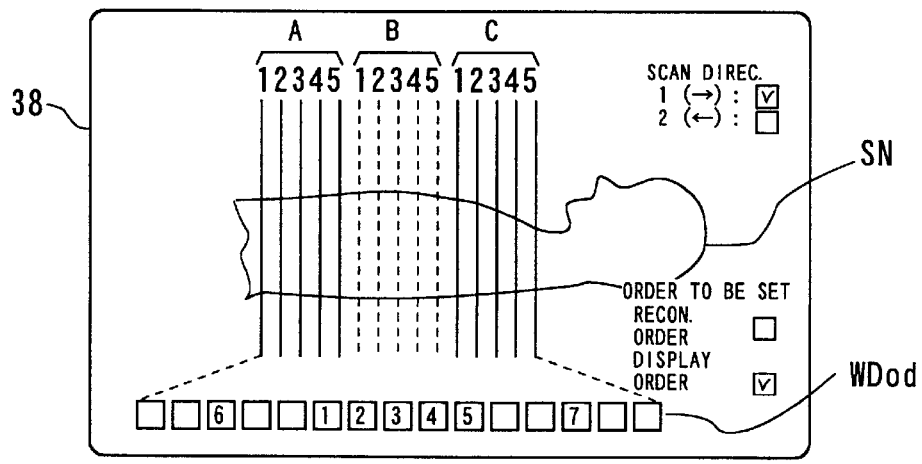
FIG. 29 is a scan plan image for explaining manual setting of another order of display in a second modification of the twelfth embodiment.

Corresponding to steps 66 to 68 in FIG. 23, the main controller 30 displays on the display 38 a plurality of windows WDod each associating with each of the slice positions for all the scans, as shown in FIG. 28 or 29. Into any one or more windows WDod, cardinal numerals 1, 2, 3, . . . are given in an arbitrary order (i.e., at regular or random slice intervals) with a keyboard or others. The main controller 30 recognizes the reconstruction or display order in agreement with the ascendant order of the numerals (1, 2, 3, . . . ).

FIGS. 28 and 29 are examples showing finally set display orders. Both are set for the scan direction "1". In FIG. 28, among a total of 25 slices obtained by three scans A, B and C, slices positioning at both the end sides in the slice direction are displayed at coarse slice intervals, while slices in the central portion thereof (corresponding to scan B) are displayed at a finer slice interval. The images of those selected slices are displayed in turn according to a specified scan direction. This setting is particularly convenient when it is known in advance that a region of interest of a disease positions in the center within a scanned region. In the case of FIG. 29, the images of slices which position in the center within a scanned region are displayed at first in the order complying with a specified scan direction, before those of slices in both the end sides thereof are displayed. This setting manner is useful where it is known that a diagnostically interested region is in the center of a scanned region and its display is the top priority; on one hand, it is enough that both the sided slices are only confirmed. This display technique is different in part from the invention, but still effective in giving a top priority to the display of medically interested parts.

Additionally, if required, separately from in which way the scan direction is set, the image-display order may be manually set totally at random, dependent on conditions concerning a region of diagnostic interest of a patient.

As described above, an operator is allowed to specify an arbitrary or random image-display order on the display through setting the reconstruction order or the display order itself. Thus the image-display order can almost completely adapt to changes in diagnostically interested regions and/or each patient. Further, the image-display thus-set can be confirmed there, providing flexibility in an immediate alteration thereof.

As a further variation, in the forgoing embodiments and modifications, the multiple scan of the present invention can be performed using only part of the detecting element rows of the detector, of which partial detecting element rows are defined by narrowing the opening of the pre-collimator.

Although the description above contains many specificities, these should not be construed as limiting the scope of the invention but as merely providing illustrations of some of the presently preferred embodiments of this invention. Thus the scope of this invention should be determined by the appended claims and their legal equivalents.

What I claim is:

1. A diagnostic system in which a plurality of frames of tomographic images of an object obtained based on multi-slice/multi-scan imaging are successively displayed on a display unit in parallel with an operation for scanning the object, the multi-slice/multi-scan imaging being carried out so that multi-slices of the object are scanned at a time with the whole multi-slices shifted scan by scan in positions along a given direction, comprising:

means for specifying a production order on which the plurality of frames of tomographic images are produced, the production order depending on the given direction;

means for performing the multi-slice/multi-scan imaging of the object so as to acquire data from the multi-slices of the object;

means for producing the plurality of frames of tomographic images from the acquired data in the specified production order; and means for displaying on the display unit at least one of the plurality of frames of tomographic images each time one frame of the tomographic images is produced by the producing means.

2. The system of claim 1, wherein the displaying means displays on the display unit the plurality of frames of tomographic images as a list of images in which the plurality of frames of tomographic images are displayed according to the specified production order.

3. The system of claim 1, wherein the producing means includes binding means for mutually binding at least two contiguous frames of tomographic images residing in the plurality of frames of tomographic images into one combined frame of tomographic image by mutually adding image data thereof, and the displaying means includes means for displaying the one combined frame of tomographic image.

4. The system of claim 1, wherein the production order specified by the specifying means is in accord with the given direction along which sliced positions of the multi-slices are moved every scan.

5. The system of claim 4, wherein the given direction is a direction along which at least one of a tabletop on which the object lies and a gantry in which the performing means is provided is moved every scan.

6. The system of claim 1 which is configured as an X-ray CT scanner of multi-slice type, wherein the X-ray CT scanner includes, as the performing means, an X-ray source irradiating an X-ray beam toward the object, a two-dimensional detector in which a plurality of arrays of detecting elements are arranged in a direction made to be in accord with the given direction during the imaging, the detecting elements being for detecting the X-ray beam transmitted through the object, and data acquisition means for acquiring and outputting, as the data from the multi-slices, projection data corresponding to a signal detected by the two-dimensional detector; and the X-ray CT scanner includes, as the producing means, reconstructing means for reconstructing the plurality of frames of tomographic images from the projection data.

7. The system of claim 6, wherein the specifying means includes means for setting a reconstruction order of the plurality of frames of tomographic images to be reconstructed by the reconstructing means.

8. A diagnostic system in which a plurality of frames of tomographic images of an object obtained based on multi-slice/multi-scan imaging are successively displayed on a display unit in parallel with an operation for scanning the object, the multi-slice/multi-scan imaging being carried out so that multi-slices of the object are scanned at a time with the whole multi-slices shifted scan by scan in positions along a given direction, comprising:

means for specifying a display order on which the plurality of frames of tomographic images are displayed, the display order depending on the given direction;

means for performing the multi-slice/multi-scan imaging of the object so as to acquire data from the multi-slices of the object;

means for producing the plurality of frames of tomographic images from the acquired data; and means for displaying on the display unit at least one of the plurality of frames of tomographic images in the specified display order each time one frame of the tomographic images is produced by the producing means.

9. The system of claim 8, wherein the displaying means displays on the display unit the plurality of frames of tomographic images as a list of images in which the plurality of frames of tomographic images are displayed according to the display order.

10. The system of claim 8, wherein the displaying means displays on the display unit the plurality of frames of tomographic images one by one in turn according to the specified display order.

11. The system of claim 8, wherein the producing means comprises binding means for mutually binding at least two contiguous frames of tomographic images residing in the plurality of frames of tomographic images into one combined frame of tomographic image by mutually adding image data thereof, and the displaying means includes means for displaying the one combined frame of tomographic image.

12. The system of claim 8, wherein the display order specified by the specifying means is in accord with the given direction along which sliced positions of the multi-slices are moved every scan.

13. The system of claim 12 which is configured as an X-ray CT scanner of multi-slice type, wherein the X-ray CT scanner includes, as the performing means, an X-ray source irradiating an X-ray beam toward the object, a two-dimensional detector in which a plurality of arrays of detecting elements are arranged in a direction made to be in accord with the given direction during the imaging, the detecting elements being for detecting the X-ray beam transmitted through the object, and data acquisition means for acquiring and outputting, as the data from the multi-slices, projection data corresponding to a signal detected by the two-dimensional detector; and the X-ray CT scanner includes, as the producing means, reconstructing means for reconstructing the plurality of frames of tomographic images from the projection data.

14. The system of claim 12, wherein the given direction is a direction along which at least one of a tabletop on which the object lies and a gantry in which the performing means is provided is moved every scan.

15. The system of claim 14, wherein the producing means comprises binding means for mutually binding at least two contiguous frames of tomographic images residing in the plurality of frames of tomographic images into one combined frame of tomographic image by mutually adding image data thereof, and the displaying means includes means for displaying the combined frame of tomographic image.

16. The system of claim 15, wherein the displaying means displays on the display unit the plurality of frames of tomographic images one by one in turn according to the specified display order.

17. The system of claim 15, wherein the displaying means displays on the display unit the plurality of frames of tomographic images as a list of images in which the plurality of frames of tomographic images are displayed according to the specified display order.

18. A diagnostic system having a display unit, comprising:

means for performing scanning with an object to acquire data therefrom;

means for producing a plurality of frames of images from the data in a production order;

means for displaying on the display unit the plurality of frames of images in a display order in response to production of each of the plurality of frames of tomographic images; and means for displaying information about either one of the production order used by the image producing means and the display order used by the image displaying means.

19. The diagnostic system of claim 18, wherein the information displaying means displays the information on the display unit.

20. The diagnostic system of claim 19, further comprising means for setting either one of the production order and the display order into an arbitrary order.

21. The diagnostic system of claim 20, wherein the order setting means includes means for manually setting, as either one of the production order and the display order, information about positions to be regularly sliced of the object.

22. The diagnostic system of claim 20, wherein the order setting means manually sets as of the production order and the display order, information about positions to be randomly sliced of the object.

* * * * *